(12) United States Patent
Silberman et al.

(10) Patent No.: US 11,839,514 B2
(45) Date of Patent: Dec. 12, 2023

(54) METHODS AND APPARATUSES FOR GUIDING COLLECTION OF ULTRASOUND DATA

(71) Applicant: BFLY Operations, Inc., Guilford, CT (US)

(72) Inventors: Nathan Silberman, Brooklyn, NY (US); Igor Lovchinsky, New York, NY (US)

(73) Assignee: BFLY OPERATIONS, INC, Burlington, MA (US)

( * ) Notice: Subject to any disclaimer, the term of this patent is extended or adjusted under 35 U.S.C. 154(b) by 613 days.

(21) Appl. No.: 16/544,058

(22) Filed: Aug. 19, 2019

(65) Prior Publication Data

US 2020/0054307 A1     Feb. 20, 2020

Related U.S. Application Data

(60) Provisional application No. 62/765,314, filed on Aug. 20, 2018.

(51) Int. Cl.
    *G06N 3/02*      (2006.01)
    *A61B 8/08*      (2006.01)
    *A61B 8/00*      (2006.01)

(52) U.S. Cl.
    CPC .......... *A61B 8/5207* (2013.01); *A61B 8/0883* (2013.01); *A61B 8/461* (2013.01); *A61B 8/565* (2013.01); *G06N 3/02* (2013.01)

(58) Field of Classification Search
    CPC .................................................. A61B 8/5207
    See application file for complete search history.

(56) References Cited

U.S. PATENT DOCUMENTS 10,628,932 B2    4/2020   Rothberg et al.
10,706,520 B2    7/2020   Rothberg et al.
(Continued)

FOREIGN PATENT DOCUMENTS

EP           2818116 A1 * 12/2014  ......... A61B 8/4245
WO   WO 2017/222970 A1    12/2017

OTHER PUBLICATIONS

International Search Report and Written Opinion dated Oct. 25, 2019 in connection with International Application No. PCT/US2019/047028.
(Continued)

*Primary Examiner* — Oneal R Mistry
(74) *Attorney, Agent, or Firm* — Boston & Galway

(57) ABSTRACT

Aspects of the technology described herein relate to displaying indications of anatomical regions that have been imaged and/or that should be imaged next. In some embodiments, ultrasound data collected from a subject by an ultrasound device may be received, an automatic determination may be made that the ultrasound data was collected from a particular anatomical location, and an indication of the anatomical location may be displayed. In some embodiments, a plurality of anatomical locations may be determined for imaging, an anatomical location from among the plurality of anatomical locations may be automatically selected, and an indication of the anatomical location may be displayed. Displaying an indication of an anatomical location may include displaying or modifying a marker on a frame of a video of the subject such that the marker appears in the frame of the video to be located at the anatomical location on the subject.

8 Claims, 17 Drawing Sheets

(56) References Cited

U.S. PATENT DOCUMENTS

| | | | |
|---|---|---|---|
| 2010/0049050 A1 | 2/2010 | Pelissier et al. | |
| 2010/0305428 A1 | 12/2010 | Bonner et al. | |
| 2011/0055447 A1 | 3/2011 | Costa | |
| 2011/0306025 A1* | 12/2011 | Sheehan | A61B 8/58 434/267 |
| 2012/0071758 A1* | 3/2012 | Lachaine | A61N 5/1049 600/443 |
| 2013/0079627 A1 | 3/2013 | Lee | |
| 2013/0237811 A1 | 9/2013 | Mihailescu et al. | |
| 2016/0171708 A1 | 6/2016 | Kim et al. | |
| 2017/0265843 A1* | 9/2017 | Abe | A61B 8/14 |
| 2017/0360401 A1 | 12/2017 | Rothberg et al. | |
| 2017/0360403 A1 | 12/2017 | Rothberg et al. | |
| 2017/0360412 A1 | 12/2017 | Rothberg et al. | |
| 2018/0225993 A1 | 8/2018 | Buras et al. | |
| 2018/0308247 A1* | 10/2018 | Gupta | G01N 29/44 |
| 2019/0000318 A1 | 1/2019 | Caluser | |
| 2019/0008476 A1* | 1/2019 | Erkamp | A61B 8/0841 |
| 2019/0130554 A1 | 5/2019 | Rothberg et al. | |
| 2019/0142388 A1 | 5/2019 | Gonyeau et al. | |
| 2019/0196600 A1 | 6/2019 | Rothberg et al. | |
| 2019/0266716 A1 | 8/2019 | Rothberg et al. | |
| 2019/0282208 A1 | 9/2019 | Silberman et al. | |
| 2019/0307428 A1 | 10/2019 | Silberman et al. | |
| 2020/0015781 A1* | 1/2020 | Hendriks | A61B 34/10 |
| 2020/0037986 A1 | 2/2020 | Silberman et al. | |
| 2020/0037987 A1 | 2/2020 | Silberman et al. | |
| 2020/0037998 A1 | 2/2020 | Gafner et al. | |
| 2020/0046322 A1 | 2/2020 | Silberman | |
| 2020/0060658 A1 | 2/2020 | Gafner et al. | |
| 2020/0187901 A1* | 6/2020 | Suresh | G06T 7/0012 |
| 2020/0211174 A1 | 7/2020 | Rothberg et al. | |
| 2020/0214672 A1 | 7/2020 | de Jonge et al. | |
| 2020/0214674 A1 | 7/2020 | Gafner et al. | |
| 2020/0214679 A1 | 7/2020 | Silberman et al. | |
| 2021/0030392 A1* | 2/2021 | Dmitrieva | A61B 8/463 |

OTHER PUBLICATIONS

Lee et al., Identifying multiple abdominal organs from CT image series using a multimodule contextual neural network and spatial fuzzy rules. IEEE Transactions of Information Atechnology in Biomedicine. Sep. 8, 2003;7(3):208-217.

Poonguzhali et al., Automatic Classification of Focal Lesions in Ultrasound Liver Images Using Combined Texture Features. Information Technology Journal. Dec. 31, 2008;7(1):205-209.

International Preliminary Report on Patentability dated Mar. 4, 2021 in connection with International Application No. PCT/US2019/047028.

Extended European Search Report for European Application No. 19852022.3, dated Mar. 29, 2022.

Office Communication dated Jul. 2, 2021 for U.S. Appl. No. 16/533,090.

Office Communication dated Oct. 28, 2021 for U.S. Appl. No. 16/533,090.

Office Communication dated Apr. 18, 2022 for U.S. Appl. No. 16/533,090.

U.S. Appl. No. 16/533,090, filed Aug. 6, 2019, Silberman.

* cited by examiner

METHODS AND APPARATUSES FOR GUIDING COLLECTION OF ULTRASOUND DATA

CROSS-REFERENCE TO RELATED APPLICATIONS

The present application claims the benefit under 35 U.S.C. § 119(e) of U.S. Provisional Patent Application Ser. No. 62/765,314, filed Aug. 20, 2018, and entitled "METHODS AND APPARATUSES FOR GUIDING COLLECTION OF ULTRASOUND DATA," which is hereby incorporated herein by reference in its entirety.

FIELD

Generally, the aspects of the technology described herein relate to guiding collection of ultrasound data.

BACKGROUND

Ultrasound devices may be used to perform diagnostic imaging and/or treatment, using sound waves having frequencies that are higher than those audible to humans. Ultrasound imaging may be used to see internal soft tissue body structures, for example to find a source of disease or to exclude any pathology. When ultrasound pulses are transmitted into tissue (e.g., by using an ultrasound device), sound waves are reflected by the tissue, with different tissues reflecting varying degrees of sound. These reflected sound waves are then recorded and processed to form an ultrasound image which is displayed to an operator. The strength (e.g., amplitude) of the sound signal and the time it takes for the sound wave to travel through the body provide information used to produce the ultrasound image. Many different types of images can be formed using ultrasound devices including, for example, images that show two-dimensional cross-sections of tissue, blood flow, motion of tissue over time, the location of blood, the presence of specific molecules, the stiffness of tissue, and/or the anatomy of a three-dimensional region.

SUMMARY

According to one aspect, a method comprises receiving, by a processing device in operative communication with an ultrasound device, first ultrasound data collected from a subject by the ultrasound device; automatically determining, based on the first ultrasound data, a first anatomical location on the subject from which at least some of the first ultrasound data was collected; and displaying, on a non-ultrasound image or video, a first indication of the first anatomical location.

In some embodiments, automatically determining the first anatomical location on the subject from which at least some of the first ultrasound data was collected comprises inputting the first ultrasound data to a statistical model trained to accept ultrasound data as an input and determine an anatomical location from which the ultrasound data was collected. In some embodiments, the statistical model comprises a convolutional neural network, a deep learning model, a random forest, a support vector machine, or a linear classifier.

In some embodiments, displaying the first indication comprises displaying a marker that was not displayed prior to automatically determining the first anatomical location on the subject from which at least some of the first ultrasound data was collected. In some embodiments, displaying the first indication comprises modifying a marker that was displayed prior to automatically determining the first anatomical location on the subject from which at least some of the first ultrasound data was collected. In some embodiments, displaying the first indication comprises displaying or modifying a marker on a frame of a video of the subject such that the marker appears in the frame of the video to be located at the first anatomical location on the subject. In some embodiments, the frame of the video is captured by a camera on the processing device. In some embodiments, displaying or modifying the marker on the frame of the video of the subject comprises determining which portion of the frame of the video depicts the first anatomical location. In some embodiments, determining which portion of the frame of the video depicts the first anatomical location comprises inputting the frame of the video to a statistical model trained to accept a frame of video and determine portions of the frame of the video that depict anatomical locations. In some embodiments, determining which portion of the frame of the video depicts the first anatomical location comprises inputting the frame of the video to a statistical model trained to accept a frame of video and determine a pose of a camera that captured the frame of the video relative to the subject. In some embodiments, the method further comprises integrating over time portions of successive frames of the video depicting the first anatomical location. In some embodiments, integrating over time the portions of the successive frames of the video depicting the first anatomical location comprise using a motion and/or orientation sensor on the processing device. In some embodiments, the statistical model comprises a convolutional neural network, a deep learning model, a random forest, a support vector machine, or a linear classifier. In some embodiments, determining which portion of the frame of the video depicts the first anatomical location comprises detecting, in the frame of the video, fiducial markers indicating one or more edges and/or one or more vertices of the first anatomical location. In some embodiments, displaying or modifying the marker on the frame of the video comprises displaying an outline on the frame of the video that surrounds the first anatomical location. In some embodiments, displaying or modifying the marker on the frame of the video comprises displaying a filled in outline on the frame of the video that surrounds the first anatomical location and that was not filled in prior to automatically determining the first anatomical location on the subject from which at least some of the first ultrasound data was collected.

In some embodiments, the method further comprises updating a position of the marker in subsequent frames of the video such that the marker appears in the subsequent frames of the video to be located at the first anatomical location on the subject. In some embodiments, the marker and the frame of the video comprise an augmented reality interface. In some embodiments, displaying the first indication comprises displaying or modifying a marker on an image of a body or a body portion such that the marker appears in the image of the body or body portion to be located at the first anatomical location on the subject. In some embodiments, the image of the body or body portion does not change as the processing device moves. In some embodiments, displaying the first indication comprises displaying or modifying text describing the first anatomical location. In some embodiments, displaying the first indication comprises displaying a symbol next to the text describing the first anatomical location. In some embodiments, displaying the first indication comprises striking through the text describing the first anatomical location. In some embodiments, displaying the first indication comprises displaying or modifying an image of the first anatomical location. In some embodiments, displaying the first indication comprises displaying a symbol next to the image of the first anatomical location. In some embodiments, displaying the first indication comprises striking through the image of the first anatomical location. In some embodiments, the first anatomical location comprises a region of a lung. In some embodiments, the first anatomical location comprises an anatomical location imaged as part of an imaging protocol. In some embodiments, displaying the first indication of the first anatomical location comprises displaying an augmented reality interface. In some embodiments, the method further comprises receiving, by the processing device, second ultrasound data collected from the subject by the ultrasound device; automatically determining, based on the second ultrasound data, a second anatomical location on the subject from which at least some of the second ultrasound data was collected; and simultaneously displaying the first indication of the first anatomical location and a second indication of the second anatomical location.

According to another aspect, a method comprises determining a plurality of anatomical locations on a subject for imaging; automatically selecting a first anatomical location from among the plurality of anatomical locations; and displaying, by a processing device in operative communication with an ultrasound device, a first indication of the first anatomical location.

In some embodiments, determining the plurality of anatomical locations on the subject for imaging comprises automatically determining the plurality of anatomical locations on the subject for imaging. In some embodiments, determining the plurality of anatomical locations on the subject for imaging is based on a user selection of an anatomical region to be imaged. In some embodiments, the anatomical region comprises a lung. In some embodiments, determining the plurality of anatomical locations on the subject for imaging is based on a user selection of an imaging protocol.

In some embodiments, automatically selecting the first anatomical location from among the plurality of anatomical locations comprises selecting an anatomical location that is first in an ordering of the plurality of anatomical locations. In some embodiments, automatically selecting the first anatomical location from among the plurality of anatomical locations comprises selecting the first anatomical location at random from the plurality of anatomical locations.

In some embodiments, displaying the first indication comprises displaying a marker that was not displayed prior to automatically selecting the first anatomical location from among the plurality of anatomical locations. In some embodiments, displaying the first indication comprises modifying a marker that was displayed prior to automatically selecting the first anatomical location from among the plurality of anatomical locations. In some embodiments, displaying the first indication comprises displaying or modifying a marker on a frame of a video of the subject such that the marker appears in the frame of the video to be located at the first anatomical location on the subject. In some embodiments, the frame of the video is captured by a camera on the processing device. In some embodiments, displaying or modifying the marker on the frame of the video of the subject comprises determining which portion of the frame of the video depicts the first anatomical location. In some embodiments, determining which portion of the frame of the video depicts the first anatomical location comprises inputting the frame of the video to a statistical model trained to accept a frame of video and determine portions of the frame of the video that depict anatomical locations. In some embodiments, determining which portion of the frame of the video depicts the first anatomical location comprises inputting the frame of the video to a statistical model trained to accept a frame of video and determine a pose of a camera that captured the frame of the video relative to the subject. In some embodiments, the method further comprises integrating over time portions of successive frames of the video depicting the first anatomical location. In some embodiments, integrating over time the portions of the successive frames of the video depicting the first anatomical location comprise using a motion and/or orientation sensor on the processing device. In some embodiments, the statistical model comprises a convolutional neural network, a deep learning model, a random forest, a support vector machine, or a linear classifier. In some embodiments, determining which portion of the frame of the video depicts the first anatomical location comprises detecting, in the frame of the video, fiducial markers indicating one or more edges and/or one or more vertices of the first anatomical location. In some embodiments, displaying or modifying the marker on the frame of the video comprises displaying an outline on the frame of the video that surrounds the first anatomical location. In some embodiments, displaying or modifying the marker on the frame of the video comprises displaying a filled in outline on the frame of the video that surrounds the first anatomical location and that was not filled in prior to automatically selecting the first anatomical location from among the plurality of anatomical locations.

In some embodiments, the method further comprises updating a position of the marker in subsequent frames of the video such that the marker appears in the subsequent frames of the video to be located at the first anatomical location on the subject. In some embodiments, the marker and the frame of the video comprise an augmented reality interface. In some embodiments, displaying the first indication comprises displaying or modifying a marker on an image of a body or a body portion frame of a video of the subject such that the marker appears in the image of the body or body portion to be located at the first anatomical location on the subject. In some embodiments, the image of the body or body portion does not change as the processing device moves. In some embodiments, displaying the first indication comprises displaying or modifying text describing the first anatomical location. In some embodiments, displaying the first indication of the first anatomical location comprises displaying an augmented reality interface. In some embodiments, the method further comprises receiving ultrasound data collected from the subject by the ultrasound device; automatically determining, based on the ultrasound data, that the ultrasound data was collected from the first anatomical location on the subject; and automatically selecting a second anatomical location from among the plurality of anatomical locations, where the second anatomical location is different from the first anatomical location. In some embodiments, the method further comprises receiving ultrasound data collected from the subject by the ultrasound device; and automatically determining, based on the ultrasound data, that the ultrasound data was collected from the first anatomical location on the subject; wherein automatically determining that the ultrasound data was collected from the first anatomical location on the subject comprises inputting the ultrasound data to a statistical model trained to accept ultrasound data as an input and determine an anatomical location where the ultrasound data was collected. In some embodiments, the statistical model comprises a convolutional neural network, a deep learning model, a random forest, a support vector machine, or a linear classifier.

In some embodiments, the method further comprises receiving ultrasound data collected from the subject by the ultrasound device; automatically determining, based on the ultrasound data, that the ultrasound data was collected from the first anatomical location on the subject; and responsive to automatically determining that the ultrasound data was collected from the first anatomical location on the subject, removing the first indication from display. In some embodiments, the method further comprises receiving ultrasound data collected from the subject by the ultrasound device; automatically determining, based on the ultrasound data, that the ultrasound data was collected from the first anatomical location on the subject; and responsive to automatically determining that the ultrasound data was collected from the first anatomical location on the subject, displaying a second indication of the first anatomical location, where the second indication is different from the first indication. In some embodiments, displaying the second indication comprises displaying the second indication in a different location on a display screen from the first indication. In some embodiments, displaying the second indication comprises modifying the first indication. In some embodiments, modifying the first indication comprises modifying an appearance of the first indication. In some embodiments, the method further comprises simultaneously displaying the second indication of the first anatomical location and a third indication of the second anatomical location. In some embodiments, the method further comprises displaying a second indication of the second anatomical location.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
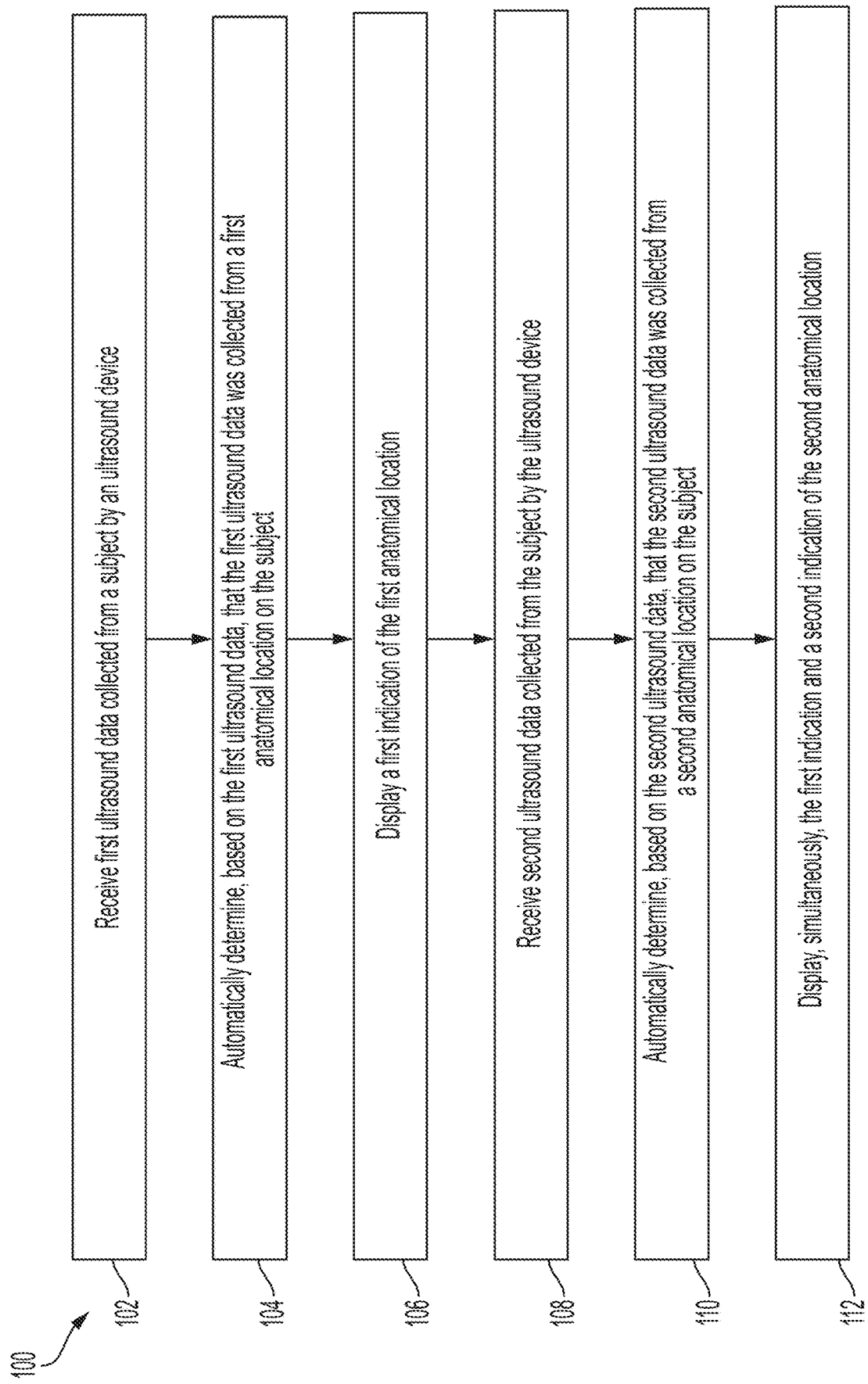
FIG. 1 illustrates an example process for guiding collection of ultrasound data, in accordance with certain embodiments described herein.

In some cases, a particular ultrasound imaging session may require imaging multiple anatomical locations on a subject (e.g., a patient). For example, when imaging the lungs, certain guidelines suggest imaging 12 anatomical regions of the lungs, while others suggest imaging 28 anatomical regions of the lungs. As another example, the Focused Assessment with Sonography in Trauma (FAST) imaging protocol includes imaging four different anatomical regions (the pericardium, the perihepatic space, the perisplenic space, and the pericardium). It may be difficult for a user of an ultrasound device to keep track of which regions have already been imaged and/or which regions should be imaged next.

Additionally, acquisition of ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may be the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include capturing ultrasound images of the incorrect anatomical structure and capturing foreshortened (or truncated) ultrasound images of the correct anatomical structure.

The inventors have developed assistive technology for helping a user to keep track of which anatomical regions have already been imaged and/or which regions should be imaged next. The assistive technology may include an augmented reality interface for helping the user (especially a non-expert user) understand where and where not to place an ultrasound device on a subject for further imaging. In certain embodiments, a processing device running the assistive technology (e.g., a portable smartphone) may automatically determine (e.g., using a statistical model such as a convolutional neural network or other deep learning model) trained, upon receiving ultrasound data, the anatomical location on the subject from which the ultrasound data was collected, and display an indication that the anatomical location was already imaged. As more ultrasound data is collected from more anatomical locations, the processing device may simultaneously display indications for the anatomical locations. For example, displaying an indication of an anatomical location may include displaying or modifying a marker on a video of the subject, where the marker appears in the video to be located at the anatomical location on the subject. The video of the subject displayed by the processing device may be similar to the view of the subject from the user's perspective (assuming that the camera capturing the video is located relatively close to the user's eyes). Thus, by seeing the location in the video of the subject at which the indication is superimposed (e.g., on a particular region of the lungs), the user may be able to understand, when viewing the subject in the real world, where that location (e.g., particular region of the lungs) is on the subject. Because the first indication in the video of the subject may indicate that this particular region has already been imaged, the user may understand to place the ultrasound device on a different region of the subject for further imaging.

In certain embodiments, the processing device running the assistive technology may determine which anatomical locations are to be imaged. For example, if the lungs are to be imaged, the processing device may select 12 or 28 anatomical regions suggested by guidelines for imaging lungs. As another example, if the FAST protocol is being used, the processing device may select the four anatomical locations that should be imaged during the FAST protocol. The processing device may then select a particular anatomical location from the plurality of anatomical locations and display an indication that the particular anatomical location should be imaged next. Upon receiving ultrasound data, the processing device may determine that the ultrasound data was collected from the particular anatomical location, remove the indication of the particular anatomical location, and display an indication of another anatomical location from the plurality of anatomical locations. For example, displaying an indication of an anatomical location may include displaying or modifying a marker on a video of the subject, where the marker appears in the video to be located at the anatomical location on the subject. Because the indication in the video of the subject may indicate that this particular region should be imaged next, the user may understand to place the ultrasound device on that particular region of the subject for further imaging.

As referred to herein, a device displaying an item (e.g., a marker on a frame of a video) should be understood to mean that the device displays the item on the device's own display screen, or generates the item to be displayed on another device's display screen. To perform the latter, the device may transmit instructions to the other device for displaying the item or information specifying a graphical user interface to display the item.

It should be appreciated that the embodiments described herein may be implemented in any of numerous ways.

Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 illustrates an example process 100 for guiding collection of ultrasound data, in accordance with certain embodiments described herein. The process 100 may be performed by a processing device in an ultrasound system. The processing device may be, for example, a portable device (e.g., a mobile phone, a smart phone, a tablet, a laptop, a device coupled to a moveable platform like a cart, etc.) or a stationary device (e.g., a desktop computer, a rack-mounted computer, a remote server), and may be in operative communication with an ultrasound device (e.g., via a wired connection, a wireless connection, a network connection, or any suitable combination thereof).

In act 102, the processing device receives first ultrasound data collected from a subject by the ultrasound device. The processing device may receive the first ultrasound data in real-time, and the ultrasound data may therefore be collected from the current anatomical location of the ultrasound device on the subject being imaged. In some embodiments, the processing device may be considered to receive ultrasound data in real-time when a delay between changes in anatomy of a subject (e.g., a heartbeat) and changes in the same anatomy depicted by ultrasound images on the processing device is sufficiently small to be indistinguishable to a human. In some embodiments, the processing device may be considered to receive ultrasound data in real-time when the delay between transmission of ultrasound waves from the ultrasound device and appearance on the processing device of an ultrasound image generated based on reflections of the transmitted ultrasound waves is less than or equal to 200 milliseconds, less than or equal to 100 milliseconds, and/or less than or equal to 50 milliseconds. The first ultrasound data may include, for example, raw acoustical data, scan lines generated from raw acoustical data, or one or more ultrasound images generated from raw acoustical data. In some embodiments, the ultrasound device may generate scan lines and/or ultrasound images from raw acoustical data and transmit the scan lines and/or ultrasound images to the processing device. In some embodiments, the ultrasound device may transmit the raw acoustical data to the processing device and the processing device may generate the scan lines and/or ultrasound images from the raw acoustical data. In some embodiments, the ultrasound device may generate scan lines from the raw acoustical data, transmit the scan lines to the processing device, and the processing device may generate ultrasound images from the scan lines. The ultrasound device may transmit the first ultrasound data to the processing device over a wired communication link (e.g., over Ethernet cable, a Universal Serial Bus (USB) cable or a Lightning cable), over a wireless communication link (e.g., over a BLUETOOTH, WiFi, or ZIGBEE wireless communication link), or any suitable combination thereof. In some instances, the ultrasound device may transmit the first ultrasound data to the processing device over a network such as a local area network or a wide area network (e.g., the Internet). The process proceeds from act 102 to act 104.

In act 104, the processing device automatically determines, based on the first ultrasound data received in act 102, a first anatomical location on the subject from which at least some of the first ultrasound data was collected. In some embodiments, to determine the first anatomical location, the processing device may input the first ultrasound data to a statistical model. The statistical model may be a convolutional neural network or other deep learning model, a random forest, a support vector machine, a linear classifier, and/or any other statistical model. The statistical model may be trained to accept ultrasound data as an input and determine the anatomical location on the subject where the ultrasound data was collected. To train the statistical model, ultrasound data labeled with the anatomical location on the subject where the ultrasound data was collected may be inputted to the statistical model and used to modulate internal parameters of the statistical model. The first anatomical location may be, for example, an anatomical region (e.g., the anterior superior region of the right lung) or an anatomical structure (e.g., the heart). The process 100 proceeds from act 104 to act 106.

In act 106, the processing device displays a first indication of the first anatomical location. In some embodiments, displaying the first indication may include displaying a marker that indicates the first anatomical region upon determining, in act 104, that the first anatomical location on the subject has been imaged. In some embodiments, displaying the first indication may include modifying, upon determining in act 104 that the first anatomical location on the subject has been imaged, a marker that indicates the first anatomical region and which was already displayed previous to the determination in act 104.

In some embodiments, the processing device may display the first indication on a non-ultrasound image or video. For example, displaying the first indication may include displaying or modifying a marker on an optical video of the subject (more precisely, a marker on each subsequent frame of the video), where the marker appears in the video to be located at the first anatomical location on the subject. The video described here may be an optical video, and may be a real-time video of the subject. The video may be captured by a camera on the processing device, and the user of the processing device may hold the processing device in one hand such that the subject is in view of the camera of the processing device, and hold the ultrasound device on the subject with the other hand.

Displaying the marker (whether before or after the determination of act 104) may include determining which portion of each frame of the video (e.g., which group of pixels) depicts the first anatomical location. In some embodiments, to determine this, the processing device may input each frame of the video, as each frame is captured, to a statistical model. The statistical model may be a convolutional neural network or other deep learning model, a random forest, a support vector machine, a linear classifier, and/or any other statistical model. The statistical model may be trained to accept a frame of video and determine the portions of the frame of the video that depict anatomical locations (e.g., the superior anterior region of the right lung, the superior posterior region of the right lung, etc.). To train the statistical model, optical images of subjects with anatomical locations labeled on the images may be inputted to the statistical model and used to modulate internal parameters of the statistical model. For example, an image of a subject may be manually segmented to delineate various anatomical locations (e.g., the superior anterior region of the right lung, the superior posterior region of the right lung, etc.).

In some embodiments, to determine which portion of each frame of the video depicts the first anatomical location, the processing device may determine a pose of the camera that captured the video relative to the subject. In accordance with certain embodiments described herein, a three-dimensional coordinate system may be referenced to the subject and may be called the subject coordinate system. For example, the subject coordinate system may be a three-dimensional coordinate system where one axis extends along the superior-inferior direction of the subject, another axis extends along the lateral-medial direction of the subject, and the third axis is orthogonal to a plane formed by these two axes. There may further be points delineating the first anatomical location (e.g., points at the edges and/or vertices of the first anatomical location) on the subject (e.g., a typical subject), where the points have particular coordinates in the subject coordinate system.

In some embodiments, the camera that captured the video may have its own three-dimensional coordinate system, which may be called the camera coordinate system. For example, the origin of the camera coordinate system may be at the center of projection of the camera and one axis of the camera coordinate system may be the optical axis of the camera. A camera-image transformation, dependent on intrinsic characteristics of the camera (e.g., focal length, optical center, etc.), may determine how the camera coordinate system is projected onto an image coordinate system referenced to the frame of video. The image coordinate system, for example, may be a two-dimensional coordinate system within the plane of the frame of video.

The processing device may determine, for a given frame of video, a pose of the camera relative to the subject when the camera captured the frame of video. The pose of the camera relative to the subject may be a quantification of a translation and/or rotation of the camera relative to the fiducial marker. In particular, the pose of the camera relative to the subject may be a transformation quantifying a translation and/or rotation of the coordinate system referenced to the camera with respect to a coordinate system referenced to the subject. The transformation may be, for example, in the form of a matrix or a quaternion. In some embodiments, to determine the pose of the camera relative to the subject, the processing device may input the frames of video to a statistical model configured to accept a frame of video of a subject and output, based on the frame of video, a pose of the camera that collected the frame of video relative to the subject. In some embodiments, a statistical model may be configured through training to accept a frame of video of a subject and output, based on the frame of video, a pose of the camera that collected the frame of video relative to the subject. In particular, the statistical learning model may be trained on sets of training data, where each set of training data includes a frame of video of a subject and a label indicating a pose of the camera that collected the frame of video relative to the subject. The training data may be labeled manually. The statistical model may thereby learn how to output poses of cameras relative to subjects based on inputted frames of video of the subjects.

In some embodiments, using the pose of the camera relative to the subject, the processing device may calculate a subject-camera transformation that quantifies a translation and/or rotation of the camera coordinate system with respect to the subject coordinate system. The subject-camera transformation may be, for example, in the form of a matrix or a quaternion. The subject-camera transformation and the camera-image transformation may determine how to transform the points in the subject coordinate system that delineate the first anatomical location to points in the image coordinate system. In particular, the points in the image coordinate system may represent the result of applying the subject-camera transformation and the camera-image transformation to the points in the subject coordinate system (e.g., multiplying the points in the subject coordinate system by the subject-camera transformation and multiplying the result of that multiplication by the camera-image transformation, if the subject-camera transformation and the camera-image transformations are matrices). The processing device may use the points in the image coordinate system to determine which portion of each frame of the video depicts the first anatomical location.

In embodiments in which a statistical model determines which portion of each frame of the video depicts the first anatomical location, it may be helpful to integrate over time the portions of each successive frame of video corresponding to the first anatomical location. Integrating the positions of the first anatomical location may be helpful for tracking the first anatomical location with respect to movement of the processing device capturing the video. Certain software development tools for augmented reality applications, such as ARKit, provide methods for such tracking. Such methods may include using motion and/or orientation sensors on the processing device (e.g., an accelerometer and/or a gyroscope).

In some embodiments, to determine which portion of each frame of the video depicts the first anatomical location, the subject may have one or more fiducial markers adhered to his/her body. For example, the one or more fiducial markers may indicate one or more edges and/or one or more vertices of the first anatomical location, and the processing device may detect the fiducial marker(s) in each frame of the video and determine which portion of each frame of the video depicts the first anatomical location based on the fiducial markers. The fiducial markers may be markers conforming to the ArUco library for augmented reality applications.

In some embodiments, the processing device may, previous to the determination of act 104, display the video of the subject as well as markers at various anatomical locations on the video of the subject. For example, the markers may be outlines surrounding various anatomical locations (e.g., surrounding the superior anterior region of the right lung, the superior posterior region of the right lung, etc.). Displaying the first indication at act 106 may include modifying (e.g., filling in) the outline corresponding to the first anatomical location. In some embodiments, the processing device may not display markers at various anatomical locations on the video previous to the determination of act 104. Displaying the first indication at act 106 may include displaying an outline (which may or may not be filled in) corresponding to the first anatomical location. In any embodiments that display markers on a video of the subject, as each frame of video is captured, the processing device may update the positions of the markers such that the markers (and any modifications of the markers) continue to appear in subsequent frames of the video to be located at particular anatomical locations on the subject. The combination of the first indication and the video of the subject may be considered an augmented reality interface, as the video may depict objects in the real world while the first indication may not depict an object in the real world (but rather a graphic superimposed on the video).

The first indication may serve as an indication that the first anatomical region has already been imaged. Therefore, if the user is conducting an imaging session in which multiple anatomical regions (including the first anatomical region) should be imaged, the first indication may serve as an indication that the user should not image the first anatomical region next. The video of the subject displayed by the processing device may be similar to the view of the subject from the user's perspective (assuming that the camera capturing the video is located relatively close to the user's eyes). Thus, by viewing where on the video of the subject the first indication is superimposed (e.g., on a particular region of the lungs), the user may be able to understand when viewing the subject in the real world where that particular region of the lungs is on the subject. Because the first indication in the video of the subject may indicate that this particular region has already been imaged, the user may understand to place the ultrasound device on a different region of the subject for further imaging.

As another example, displaying the first indication may include displaying or modifying a marker on an image of a body or a body portion, where the marker appears in the image to be located at the first anatomical location. In some embodiments, the processing device may not display markers on the image of the body or body portion prior to the determination of act 104, and at act 106 the processing device may display a new marker such that the marker appears in the image of the body or body portion to be positioned over the first anatomical location. In some embodiments, the processing device may display markers on the image of the body or body portion prior to the determination of act 104, and at act 106 the processing device may modify a marker (e.g., fill in, place a checkmark) that appears in the image of the body or body portion to be positioned over the first anatomical location. The image of the body or body portion may be a static optical image of the body or body portion (i.e., an image that does not change as the processing device moves), may not have been captured from the particular subject being imaged, and/or may be a drawn, stylized, and/or cartoonish image of the body or body portion. In some embodiments, displaying the first indication may include modifying text describing the first anatomical location (e.g., text reading "superior anterior region of the right lung") or an image depicting the first anatomical location (e.g., an image of the heart). For example, modifying the text or image may include displaying a marker (e.g., a symbol such as a checkmark) next to the text or image, or striking through the text or image. In a similar manner as described above, displaying a marker on an image of the body or body portion and/or in conjunction with images of and/or text describing anatomical locations may help a user to identify which anatomical region on the subject the user should not image next. For example, if the first indication indicates that a particular anatomical region has already been imaged, the user may understand not to image that particular anatomical region on the subject next. Using static text/images for the first indication may be helpful as a simpler and/or more organized way to keep track of which anatomical locations have already been imaged. In some embodiments, the processing device may simultaneously display multiple indications of the first anatomical location (e.g., on a video of the subject, an image of a body or body portion, and/or in conjunction with images of and text describing anatomical locations). The process 100 proceeds from act 106 to act 108.

In act 108, the processing device receives second ultrasound data collected from the subject by the ultrasound device. Further description of receiving ultrasound data may be found with reference to act 102. The process 100 proceeds from act 108 to act 110.

In act 110, the processing device automatically determines, based on the second ultrasound data, a second anatomical location on the subject from which at least some of the second ultrasound data was collected. Further description of determining, based on ultrasound data, that the ultrasound data was collected from a particular anatomical location on a subject may be found with reference to act 104. The process 100 proceeds from act 110 to act 112.

In act 112, the processing device simultaneously displays the first indication that was displayed in act 106 as well as a second indication of the second anatomical location. Any of the embodiments of the first indication described above may apply to the second indication. Further description of displaying an indication of an anatomical location may be found with reference to act 106. As an example, simultaneously displaying the first indication and the second indication may include simultaneously modifying two markers (e.g., filling in two outlines) on a frame of a video of the subject, where the markers are located over portions of the frame of the video that depict the first and second anatomical locations. As another example, simultaneously displaying the first indication and the second indication may include placing two markers on an image of the body or a body portion such that one of the markers appears in the image to be located at the first anatomical location and the other marker appears in the image to be located at the second anatomical location. As another example, simultaneously displaying the first indication and the second indication may include displaying checkmarks next to, or striking through, two instances of text or images, one of which describes the first anatomical location and the other of which describes the second anatomical location.

The second indication may serve as an indication that the second anatomical region has already been imaged. If the user is conducting an imaging session in which multiple anatomical regions (including the first and second anatomical regions) should be imaged, the simultaneous display of the first and second indications may serve as indications that the user should not image the first or second anatomical regions next. The first and second indications may remain displayed for the duration of the imaging session. It should be appreciated that as further anatomical locations are imaged, the processing device may continue to display further indications of the anatomical locations (e.g., a third indication of a third anatomical location, a fourth indication of a fourth anatomical location, etc.), and the indications may remain displayed for the duration of the imaging session. In some embodiments, acts 108-112 may be optional.

Figure 2:
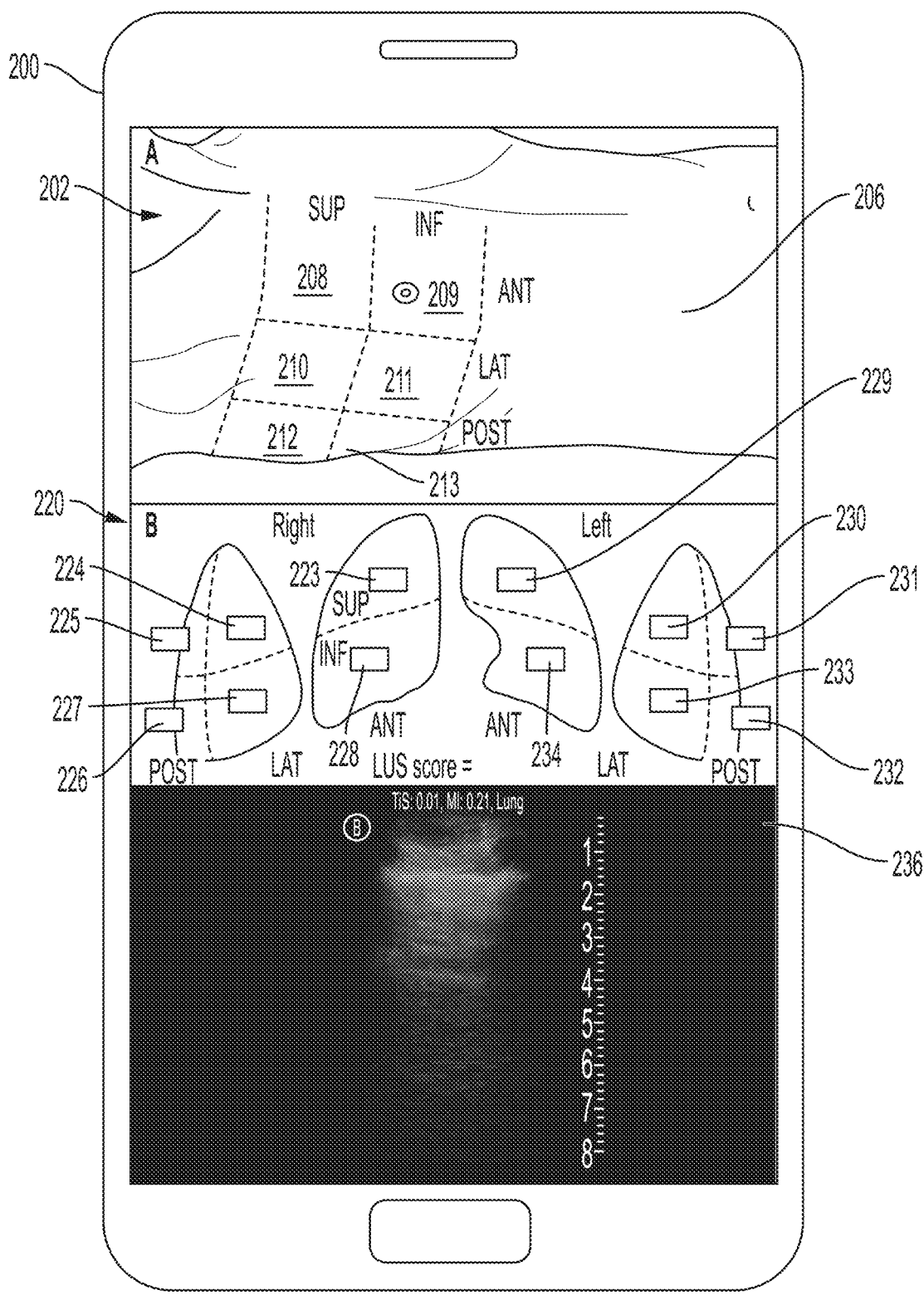
FIG. 2 illustrates an example display on a processing device prior to display of an indication of an anatomical location, in accordance with certain embodiments described herein.

FIG. 2 illustrates an example display on a processing device 200 prior to display of an indication of an anatomical location, in accordance with certain embodiments described herein. The processing device 200 displays a frame of a video 202 of a subject being imaged, a schematic depiction of the lungs 220, and an ultrasound image 236. The frame of the video 202 of the subject depicts the subject 206 and markers 208-213 of regions of the lungs. The marker 208 outlines the superior anterior region of the right lung, the marker 209 outlines the inferior anterior region of the right lung, the marker 210 outlines the superior lateral region of the right lung, the marker 211 outlines the inferior lateral region of the right lung, the marker 212 outlines the superior posterior region of the right lung, and the marker 213 outlines the inferior posterior region of the right lung.

The schematic depiction of the lungs 220 depicts markers 224-234 on regions of the lungs. The marker 223 is located at the superior anterior region of the right lung, the marker 224 is located at the superior lateral region of the right lung, the marker 225 is located at the superior posterior region of the right lung, the marker 226 is located at the inferior posterior region of the right lung, the marker 227 is located at the inferior lateral region of the right lung, the marker 228 is located at the inferior anterior region of the right lung, the marker 229 is located at the superior anterior region of the left lung, the marker 230 is located at the superior lateral region of the left lung, the marker 231 is located at the superior posterior region of the left lung, the marker 232 is located at the inferior posterior region of the left lung, the marker 233 is located at the inferior lateral region of the left lung, and the marker 234 is located at the inferior anterior region of the left lung. These regions of the lungs may be regions that should each be imaged when imaging the lungs. For example, certain guidelines suggest imaging 12 anatomical regions of the lungs, while others suggest imaging 28 anatomical regions of the lungs.

In the embodiment depicted, ultrasound image 236 represents the most recent ultrasound image collected by an ultrasound device with which the processing device 200 is in communication. The frame of the video 202 may be captured by a camera on the processing device 200 and may be the most recent frame of the video 202 collected by the camera. As described further with reference to act 106, the markers 208-213 may be determined by inputting the frame of the video 202 to a statistical model. As subsequent frames of video are captured, the markers 208-213 (as determined by the statistical model) may move to compensate for movement of the regions of the lungs in the frames of video.

Figure 3:
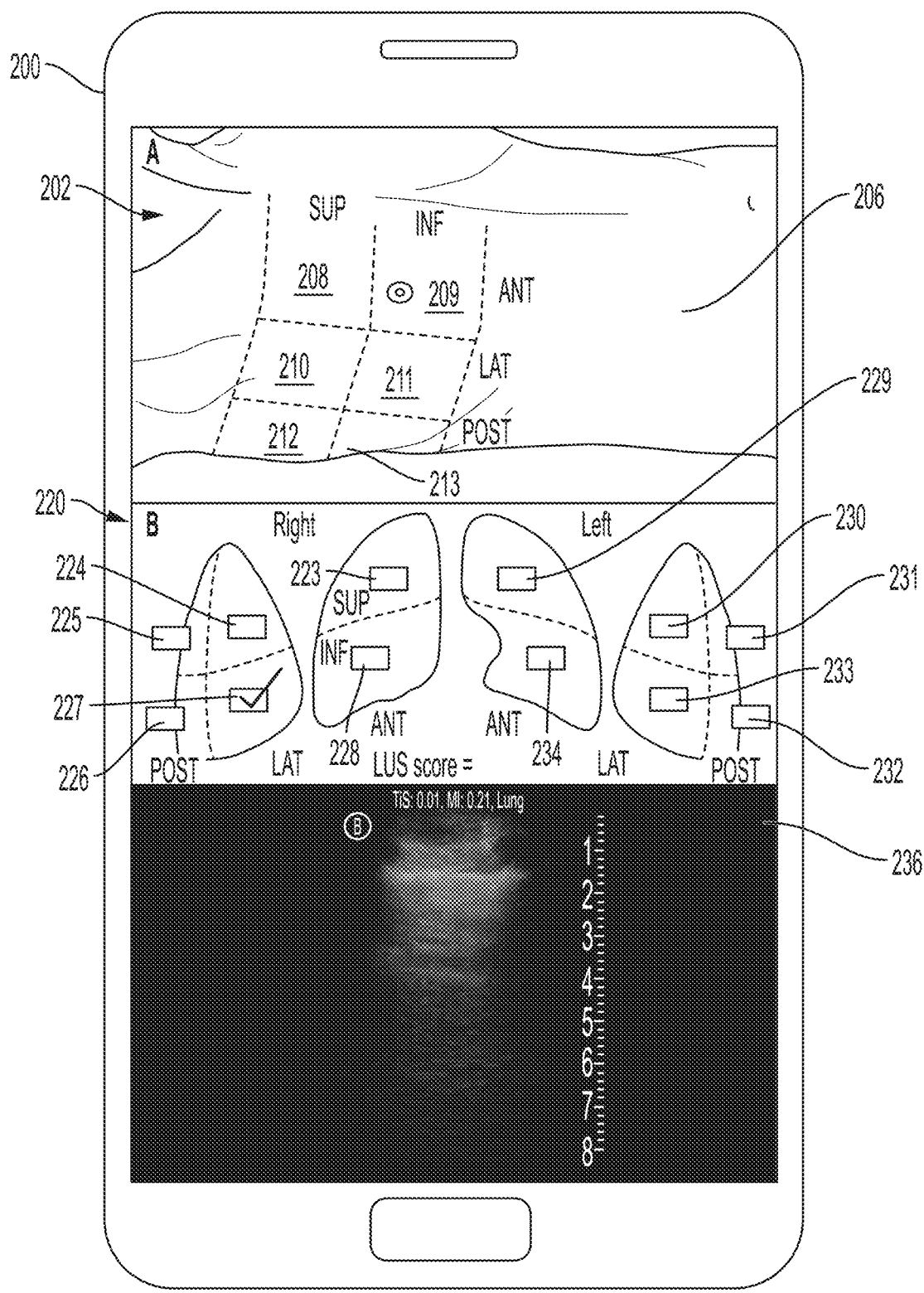
FIG. 3 illustrates an example display on a processing device displaying an indication of an anatomical location, in accordance with certain embodiments described herein.

FIG. 3 illustrates an example display on the processing device 200 displaying an indication of an anatomical location, in accordance with certain embodiments described herein. The marker 211 outlining the inferior lateral region of the right lung on the frame of the video 202 of the subject is filled in, and a checkmark is displayed on the marker 227 located at the inferior lateral region of the right lung. The filling in of the marker 211 and the checkmark on the marker 227 may both serve as an indication that the inferior lateral region of the right lung of the subject has already been imaged. Further description of displaying the first indication may be found with reference to act 106. As described with reference to act 104, the processing device may determine that the inferior lateral region of the right lung has been imaged by inputting the most recently collected ultrasound image 236 to a statistical model.

Figure 4:
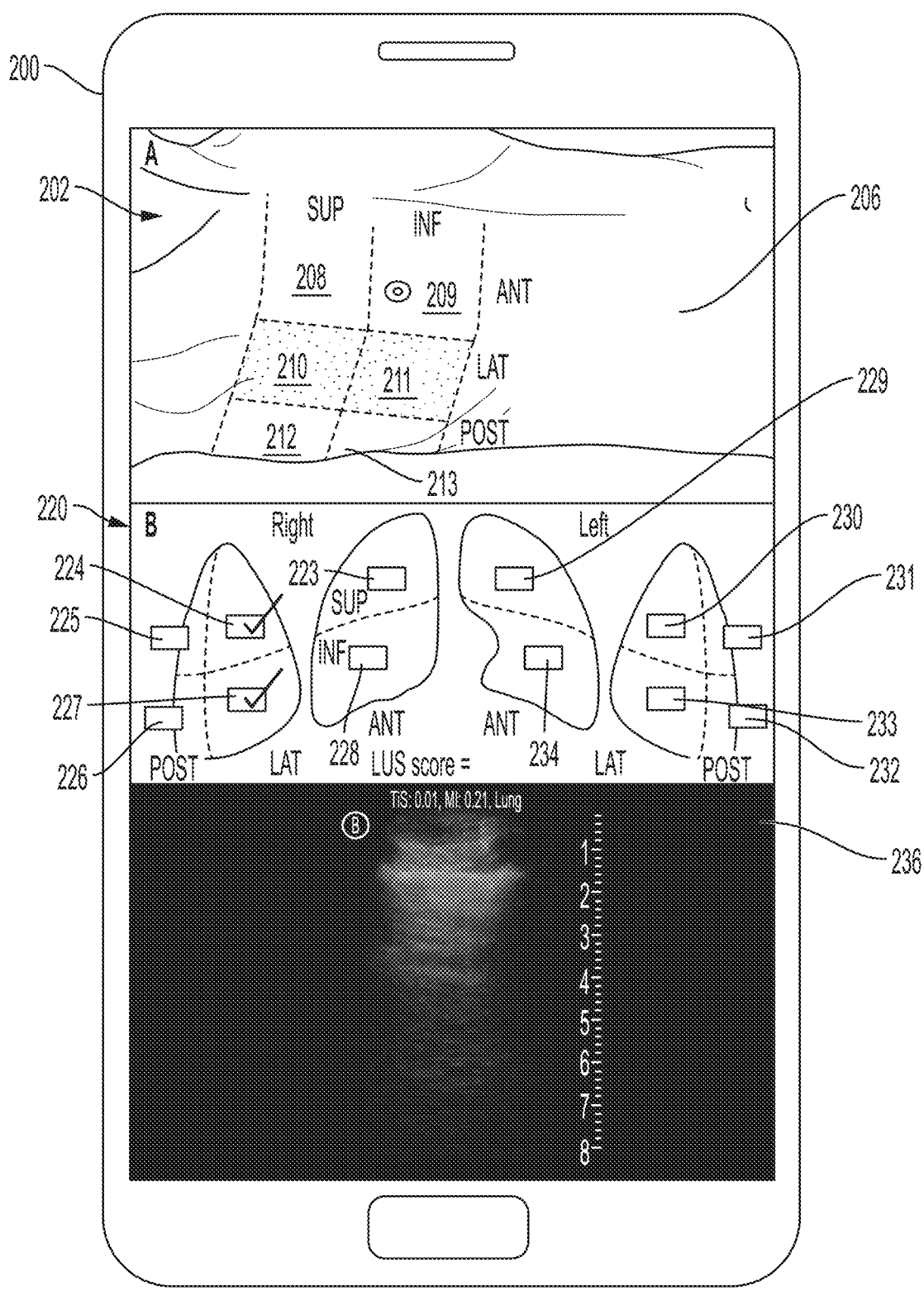
FIG. 4 illustrates an example display on a processing device simultaneously displaying two indications of two anatomical locations, in accordance with certain embodiments described herein.

FIG. 4 illustrates an example display on the processing device 200 simultaneously displaying two indications of two anatomical locations, in accordance with certain embodiments described herein. In addition to filling in the marker 211 and displaying a checkmark on the marker 227 (both of which may serve as an indication that the inferior lateral region of the right lung of the subject has already been imaged), the marker 210 outlining the superior lateral region of the right lung on the frame of the video 202 of the subject is also filled in, and a checkmark is displayed on the marker 224 located at the inferior lateral region of the right lung. The filling in of the marker 210 and the checkmark on the marker 224 may both serve as an indication that the superior lateral region of the right lung of the subject has been imaged. The processing device 200 therefore indicates that both the superior and inferior lateral regions of the right lung have already been imaged. Further description of displaying the second indication may be found with reference to act 112 of FIG. 1. As described with reference to act 110, the processing device may determine that the superior lateral region of the right lung has been imaged by inputting the most recently collected ultrasound image 236 to a statistical model.

Figure 5:
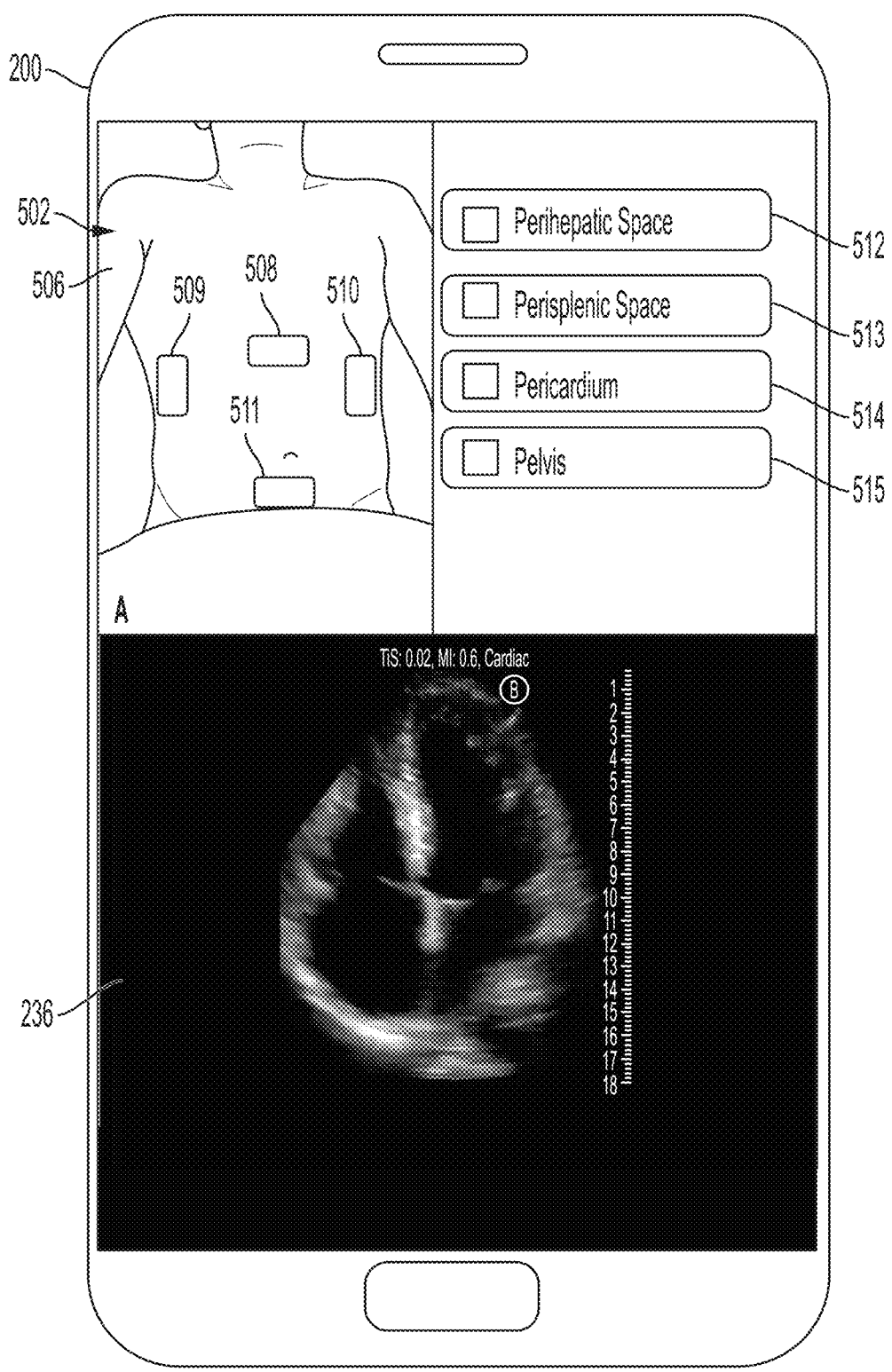
FIG. 5 illustrates an example display on a processing device prior to display of an indication of an anatomical location, in accordance with certain embodiments described herein.

FIG. 5 illustrates an example display on a processing device 200 prior to display of an indication of an anatomical location, in accordance with certain embodiments described herein. The processing device 200 displays a frame of a video 502 of a subject being imaged, checkbox options 512-515, and an ultrasound image 236. The frame of the video 502 of the subject imaged depicts the subject being imaged 506 and markers 508-51 of anatomical regions. The marker 508 is located at the pericardium, the marker 509 is located at the perihepatic space, the marker 510 is located at the perisplenic space, and the marker 511 is located at the pelvis. The checkbox option 512 includes a checkbox and text reading "Perihepatic space." The checkbox option 513 includes a checkbox and text reading "Perisplenic space." The checkbox option 514 includes a checkbox and text reading "Pericardium." The checkbox option 515 includes a checkbox and text reading "Pelvis." The perihepatic space, the perisplenic space, the pericardium, and the pelvis may be anatomical locations imaged as part of the FAST protocol.

The ultrasound image 236 may be the most recent ultrasound image collected by an ultrasound device with which the processing device 200 is in communication. The frame of the video 502 may be captured by a camera on the processing device 200 and may be the most recent frame of the video 502 captured by the camera. As described further with reference to act 106 of FIG. 1, the markers 508-511 may be determined by inputting the frame of the video 502 to a statistical model. As subsequent frames of video are captured, the markers 508-511 (as determined by the statistical model) may move to compensate for movement of the regions of the lungs in the frames of video.

Figure 6:
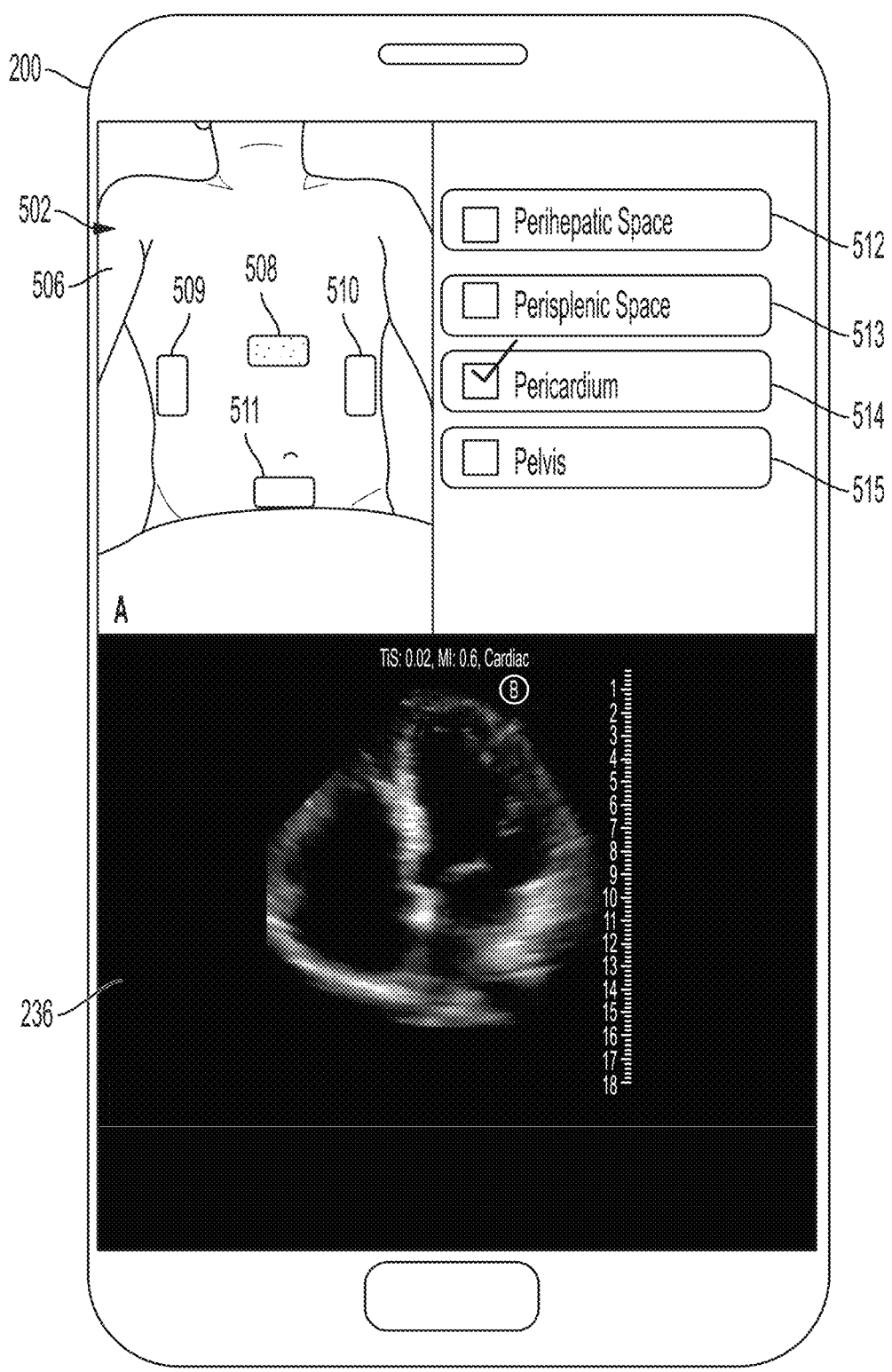
FIG. 6 illustrates an example display on a processing device displaying an indication of an anatomical location, in accordance with certain embodiments described herein.

FIG. 6 illustrates an example display on the processing device 200 displaying an indication of an anatomical location, in accordance with certain embodiments described herein. The marker 508 located at the pericardium on the frame of the video 502 of the subject is filled in, and a checkmark is displayed in the checkbox option 514 reading "Pericardium." The filling in of the marker 508 and the checkmark in the checkbox option 514 may both serve as an indication that the pericardium of the subject has already been imaged. Further description of displaying the first indication may be found with reference to act 106. As described with reference to act 104, the processing device may determine that the pericardium has been imaged by inputting the most recently collected ultrasound image 236 to a statistical model.

Figure 7:
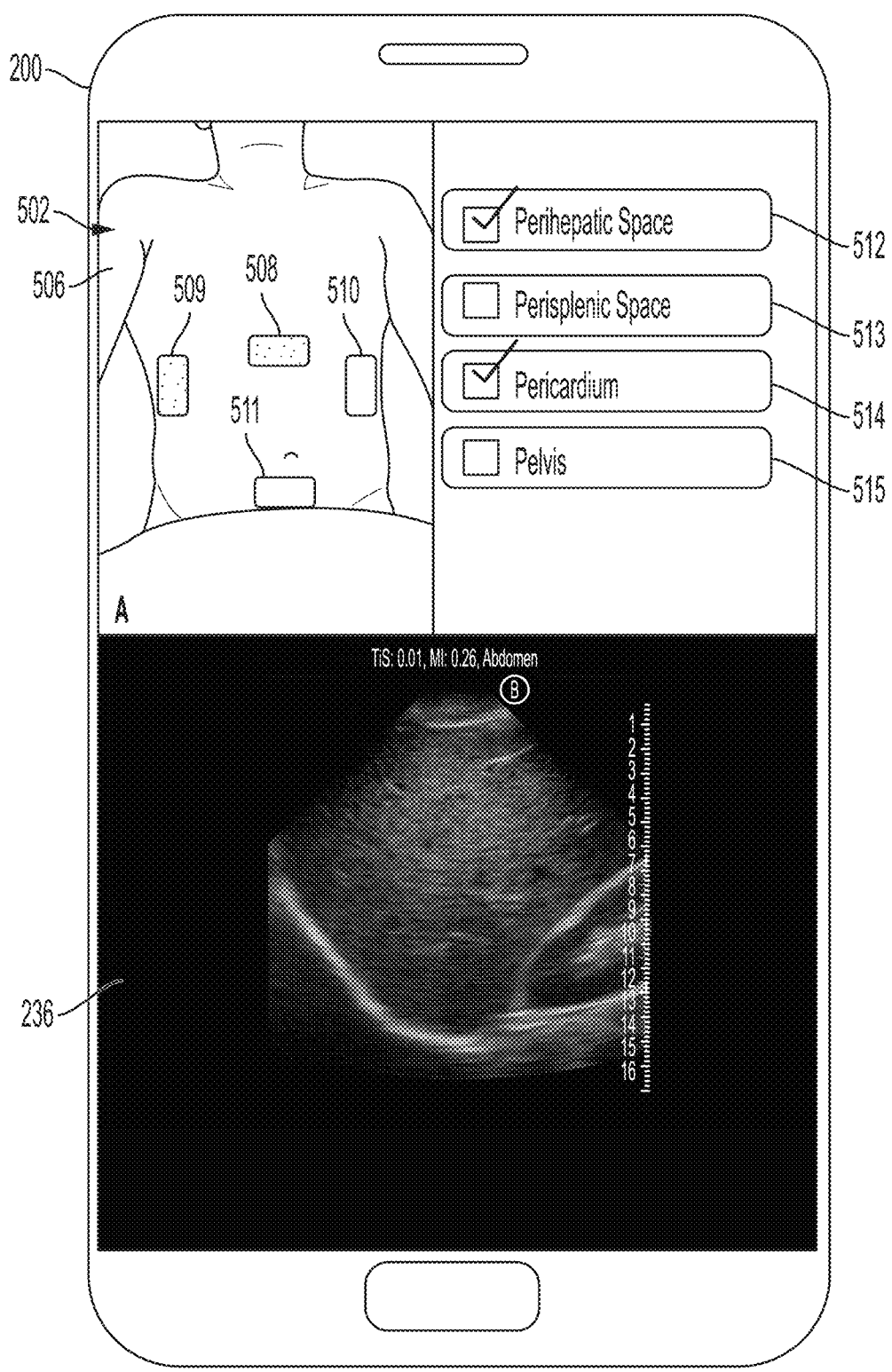
FIG. 7 illustrates an example display on a processing device simultaneously displaying two indications or two anatomical locations, in accordance with certain embodiments described herein.

FIG. 7 illustrates an example display on the processing device 200 simultaneously displaying two indications or two anatomical locations, in accordance with certain embodiments described herein. In addition to filling in the marker 508 and displaying a checkmark in the checkbox option 514, both of which may serve as an indication that the pericardium of the subject has been imaged, in FIG. 7 the marker 509 located at the perihepatic space in the frame of the video 502 of the subject is filled in, and a checkmark is displayed in the checkbox option 512 reading "Perihepatic Space." The filling in of the marker 509 and the checkmark in the checkbox option 512 may both serve as an indication that the perihepatic space of the subject has already been imaged. The processing device 200 therefore indicates that both the pericardium and the perihepatic space have already been imaged. Further description of displaying the second indication may be found with reference to act 112. As described with reference to act 110, the processing device may determine that the superior lateral region of the right lung has been imaged by inputting the ultrasound image 236 to a statistical model.

Figure 8:
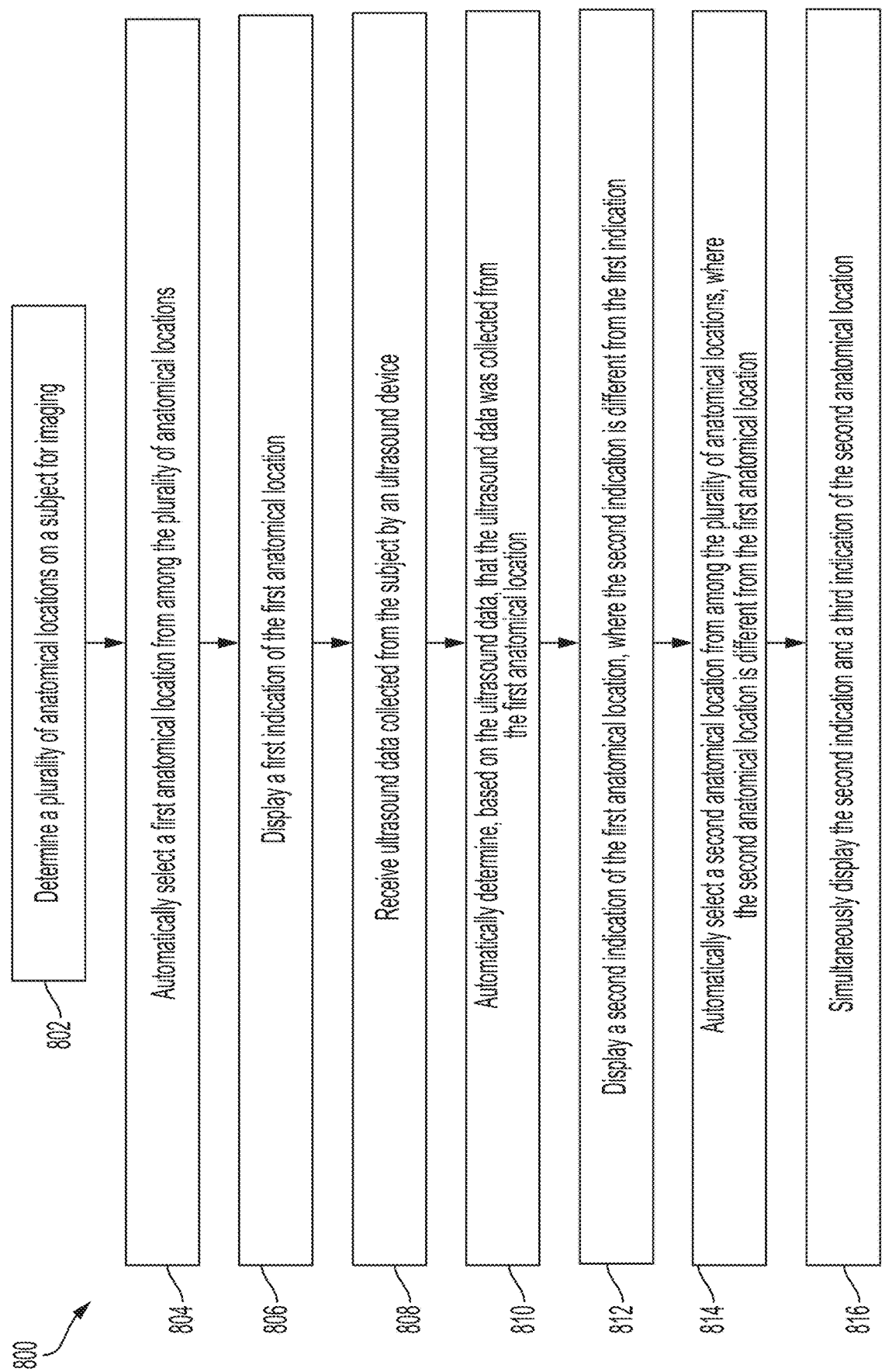
FIG. 8 illustrates an example process for guiding collection of ultrasound data, in accordance with certain embodiments described herein

FIG. 8 illustrates an example process 800 for guiding collection of ultrasound data, in accordance with certain embodiments described herein. The process 800 may be performed by a processing device in an ultrasound system. The processing device may be, for example, a portable device (e.g., a mobile phone, a smart phone, a tablet, a laptop, a device coupled to a moveable platform like a cart, etc.) or a stationary device (e.g., a desktop computer, a rack-mounted computer, a remote server), and may be in operative communication with an ultrasound device (e.g., via a wired connection, a wireless connection, a network connection, or any suitable combination thereof).

In act 802, the processing device determines a plurality of anatomical locations on a subject for imaging. In some embodiments, the processing device may determine the plurality of anatomical locations based on a user selection of an anatomical structure to be imaged. For example, if the user selects a lung imaging preset, the processing device may determine a plurality of anatomical locations that may be typically be imaged during lung imaging. In the example of lung imaging, certain guidelines suggest imaging 12 anatomical regions of the lungs, while others suggest imaging 28 anatomical regions of the lungs, etc., and these anatomical regions may constitute the plurality of anatomical locations determined by the processing device. In some embodiments, the processing device may determine the plurality of anatomical locations based on an imaging protocol. For example, if the user selects a FAST imaging preset, the processing device may determine a plurality of anatomical locations that may typically be imaged during the FAST imaging protocol. In the example of the FAST imaging protocol, the plurality of anatomical locations may constitute four anatomical locations (perihepatic space, perisplenic space, pericardium, and pelvis). The processing device may determine the plurality of anatomical locations by looking up a user-selected anatomical structure or imaging protocol in a database containing associations between anatomical structures/imaging protocols and pluralities of anatomical locations. The database may be stored on the processing device, or the processing device may access a remote server storing the database. The process 800 proceeds from act 802 to act 804.

In act 804, the processing device chooses a first anatomical location from among the plurality of anatomical locations. In some embodiments, the plurality of anatomical locations determined in 802 may be ordered, and the processing device may select the anatomical location that is first in the ordering. The plurality of anatomical locations may be ordered, for example, by proximity (e.g., successive anatomical locations in the ordering may be proximal to each other). In some embodiments, the processing device may select an anatomical location at random from the plurality of anatomical locations. The process 800 proceeds from to act 806.

In act 806, the processing device displays a first indication of the first anatomical location. In some embodiments, displaying the first indication may include displaying a marker that indicates the first anatomical region upon selecting, in act 804, the first anatomical location. In some embodiments, displaying the first indication may include modifying, upon selecting the first anatomical location in act 804, a marker that indicates the first anatomical region and which was already displayed previous to the selection in act 806.

For example, displaying the first indication may include displaying or modifying a marker on a frame of an optical video of the subject, where the first marker appears in the frame of the video to be located at the first anatomical location on the subject. As another example, displaying the first indication may include displaying or modifying a marker on an image of a body or a body portion, where the marker appears in the image to be located at the first anatomical location. In some embodiments, displaying the first indication may include modifying text describing the first anatomical location (e.g., text reading "superior anterior region of the right lung") or an image depicting the first anatomical location (e.g., an image of the heart). Further description of displaying indications of anatomical locations may be found with reference to act 106.

The first indication may serve as an indication that the first anatomical region should be imaged next. The video of the subject displayed by the processing device may be similar to the view of the subject from the user's perspective (assuming that the camera capturing the video is located relatively close to the user's eyes). Thus, by viewing where on the video of the subject the first indication is superimposed (e.g., on a particular region of the lungs), the user may be able to understand when viewing the subject in the real world where that particular region of the lungs is on the subject. Because the first indication in the video of the subject may indicate that this particular region should be imaged next, the user may understand to place the ultrasound device on that particular region of the subject for further imaging. The process 800 proceeds from act 806 to act 808.

In act 808, the processing device receives ultrasound data collected from a subject by an ultrasound device. Further description of receiving ultrasound data may be found with reference to act 102. The process 800 proceeds from act 808 to act 810.

In act 810, the processing device automatically determines, based on the ultrasound data received in act 808, that the ultrasound data was collected from the first anatomical location. Further description of this determination may be found with reference to act 104. In some embodiments, the processing device may remove the first indication from display after determining that the first anatomical location has been imaged. As the displayed indications may indicate which anatomical location the user should image next, the first indication may be removed from display as the first anatomical location has already been imaged. The process 800 proceeds from act 810 to act 812.

In act 812, the processing device displays a second indication of the first anatomical location, where the second indication is different from the first indication. In some embodiments, the second indication may be in a different portion of the processing device's display than the first indication. For example, if the processing device displayed the first indication on a video of the subject being imaged in act 806, the processing device may remove the first indication from the video but display the second indication of the first anatomical location on an image of the body or body portion or in conjunction with images of or text describing anatomical locations. In some embodiments, the second indication may be a modification of the first indication (e.g., a modification of the appearance of the first indication). For example, if the processing device displayed the first indication on a video of the subject being imaged in act 806, the processing device may display the second indication in the same location on the video of the subject as the second indication, but with a different color, shading, shape, symbol, size, etc. Any of the embodiments of the first indication described herein by be applied to the second indication. Further description of displaying indications of anatomical locations may be found with reference to act 806. The second indication of the first anatomical location may remain displayed for the duration of the imaging session and may serve as an indication that the first anatomical location has already been imaged. It should be appreciated that as further anatomical locations are imaged, the processing device may continue to display further indications of the anatomical locations, and the indications may remain displayed for the duration of the imaging session. The process 800 proceeds from act 812 to act 814.

In act 814, the processing device selects a second anatomical location from among the plurality of anatomical location, where the second anatomical location is different from the first anatomical location. As described above with reference to act 804, in some embodiments, the plurality of anatomical location determined in act 802 may be ordered, and the processing device may select the anatomical location that is after the first anatomical location in the ordering. In some embodiments, the processing device may remove the first anatomical location from the plurality of anatomical locations and select an anatomical location at random from the remaining plurality of anatomical locations. In some embodiments, the processing device may select an anatomical location at random and determine that the anatomical location was not previously selected. The process 800 proceeds from act 814 to act 816.

In act 816, the processing device simultaneously displays the second indication of the first anatomical location and a third indication of the second anatomical location. In some embodiments, the third indication may be in a different portion of the processing device's display than the second indication. For example, the processing device may display the third indication on a video of the subject being imaged in act 806 and display the second indication of the first anatomical location on an image of the body or body portion or in conjunction with images of or text describing anatomical locations. Any of the embodiments of the first indication described herein by be applied to the third indication. Further description of displaying indications of anatomical locations may be found with reference to act 806. As described above, the second indication of the first anatomical location may remain displayed for the duration of the imaging session and may serve as an indication that the first anatomical location has already been imaged. The third indication of the second anatomical location may serve as an indication to the user that the second anatomical location should be imaged next.

As described above, the first and third indications may indicate to a user which anatomical regions should be imaged next, while the second indication may indicate to the user which anatomical regions have already been imaged. In some embodiments, the process 800 may not indicate to the user which anatomical regions have already been imaged. In other words, act 812 may be absent, and the processing device may not display the second indication. In some embodiments, acts 808-816 may be absent. In some embodiments, act 816 may be absent.

Figure 9:
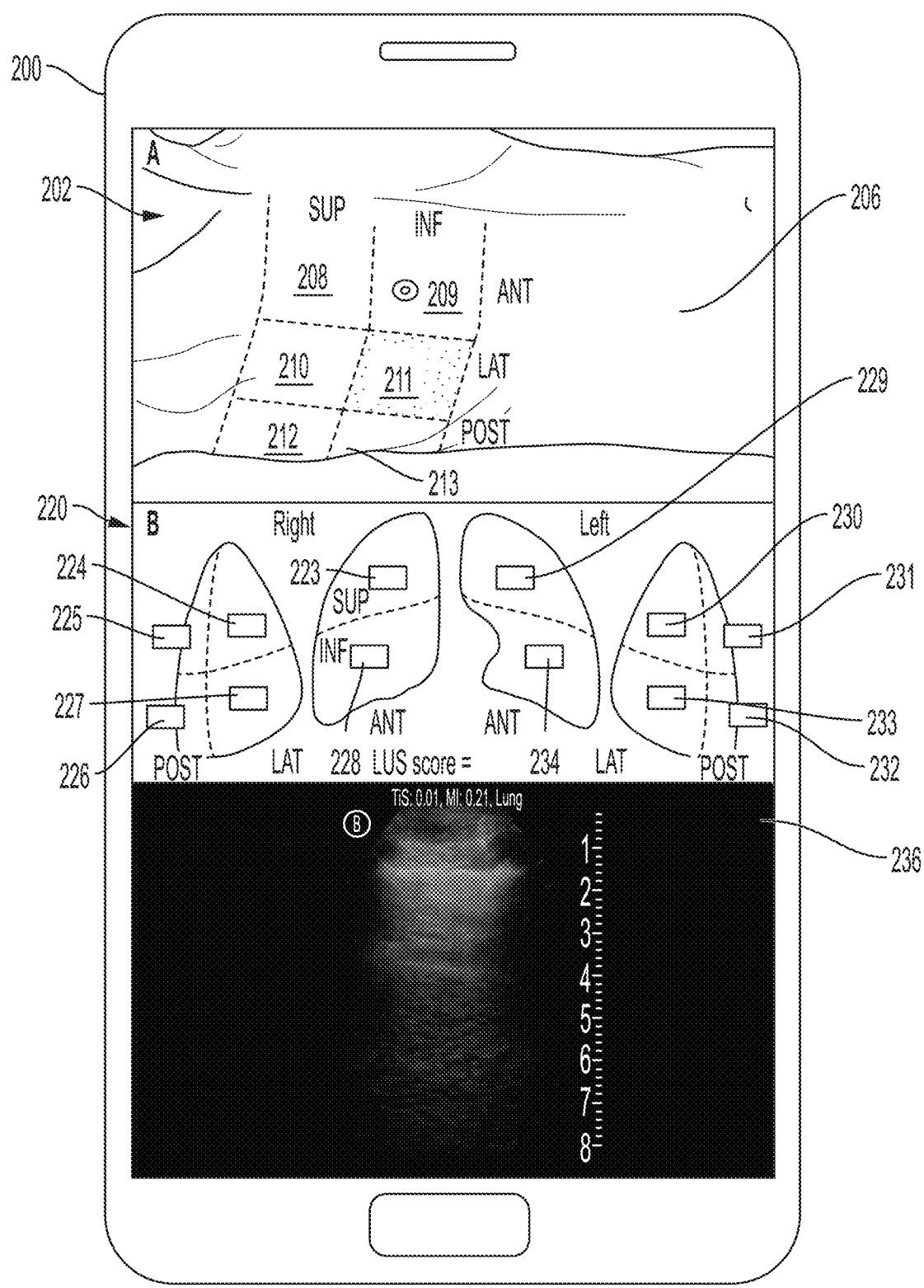
FIG. 9 illustrates an example display on a processing device displaying a first indication of an anatomical location, in accordance with certain embodiments described herein.

FIG. 9 illustrates an example display on the processing device 200 displaying a first indication of an anatomical location, in accordance with certain embodiments described herein. FIG. 9 is similar to FIG. 2 except that in FIG. 9, the marker 211 outlining the inferior lateral region of the right lung on the frame of the video 202 of the subject is filled in. The filling in of the marker 211 may serve as an indication that the inferior lateral region of the right lung of the subject should be imaged next. Further description of displaying the first indication may be found with reference to act 106.

Figure 10:
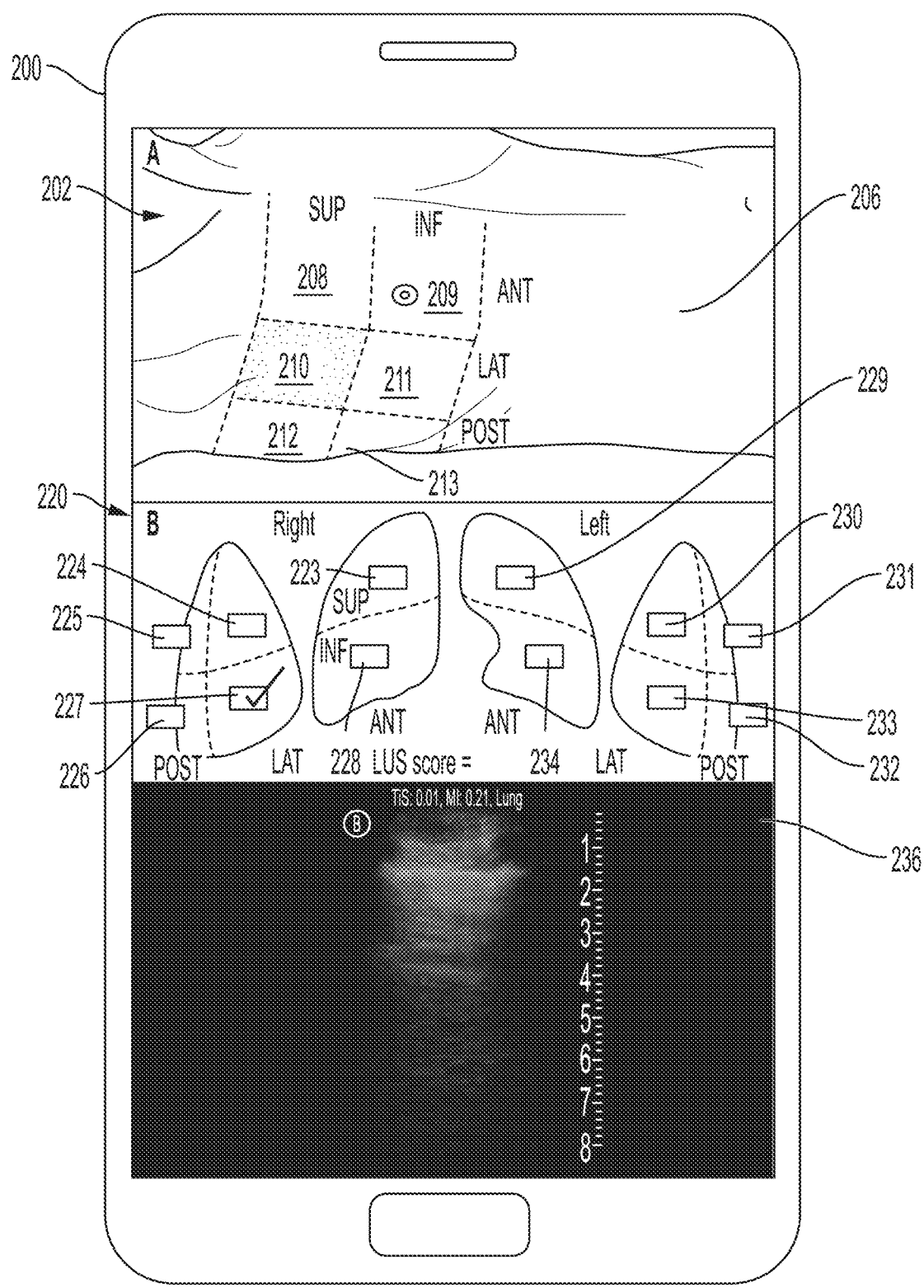
FIG. 10 illustrates an example display on a processing device simultaneously displaying two indications or two anatomical locations, in accordance with certain embodiments described herein.

FIG. 10 illustrates an example display on the processing device 200 simultaneously displaying two indications or two anatomical locations, in accordance with certain embodiments described herein. In FIG. 10, a checkmark is displayed on the marker 227, which may serve as an indication that the inferior lateral region of the right lung of the subject has been imaged. Additionally, the marker 210 outlining the superior lateral region of the right lung on the frame of the video 202 of the subject is filled in, which may serve as an indication that the superior lateral region of the right lung of the should be imaged next. Further description of displaying the second indication may be found with reference to act 112. As described with reference to act 110, the processing device may determine that the inferior lateral region of the right lung has been imaged by inputting the most recently collected ultrasound image 236 to a statistical model.

Figure 11:
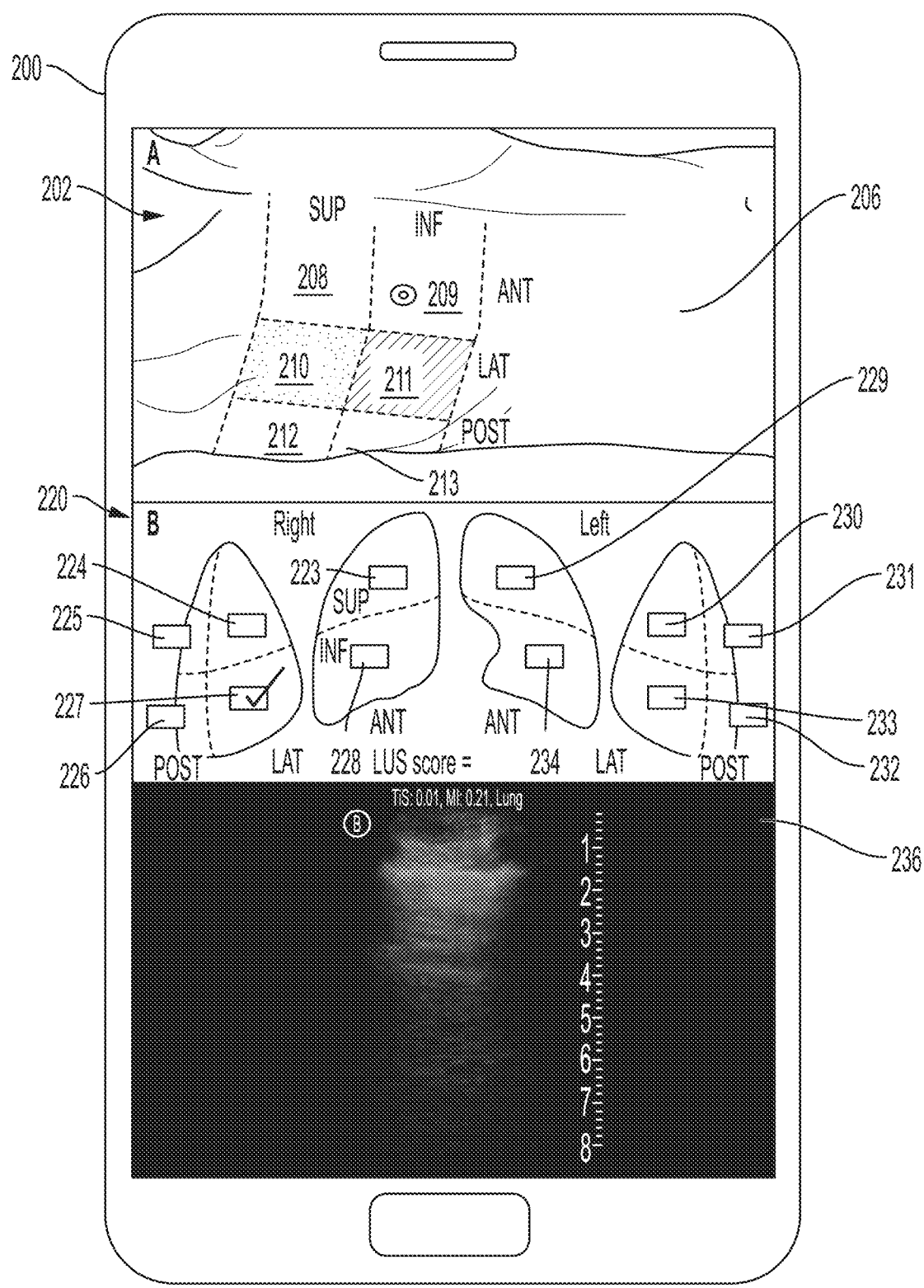
FIG. 11 illustrates an alternative to the display of FIG. 10, in accordance with certain embodiments described herein.

FIG. 11 illustrates an alternative to the display of FIG. 10, in accordance with certain embodiments described herein. In FIG. 11, the marker 211 outlining the inferior lateral region of the right lung on the frame of the video 202 of the subject is filled in, but with a different shading than the filling in of the marker 210 outlining the superior lateral region of the right lung. The filling in of the marker 211 with the different shading may serve as an indication that the inferior lateral region of the right lung has already been imaged. In other words, the filling in of the marker 211 with the different shading may distinguish it from the filling in of the marker 210 outlining the superior lateral region of the right lung, where the distinction may indicate to the user that the inferior lateral region of the right lung has already been imaged while the superior lateral region of the right lung should be imaged next. In still other words, a marker shaded in with the type of shading used for the marker 210 may indicate that the corresponding anatomical region should be imaged next while a marker shaded in with the type of shading used for the marker 210 may indicate that the corresponding anatomical region has already been imaged. The marker 211 may remain filled in for the duration of the imaging session. The filling in of the marker 211 may complement the checkmark next to the marker 227 in that both may indicate that the inferior lateral region of the right lung. Filling in the marker 211 in addition to placing the checkmark next to the marker 227 may be helpful as this may indicate to the user on the video of the subject 202 (which, as described above, may be similar to the view of the subject from the user's perspective) which anatomical region has already been imaged.

Figure 12:
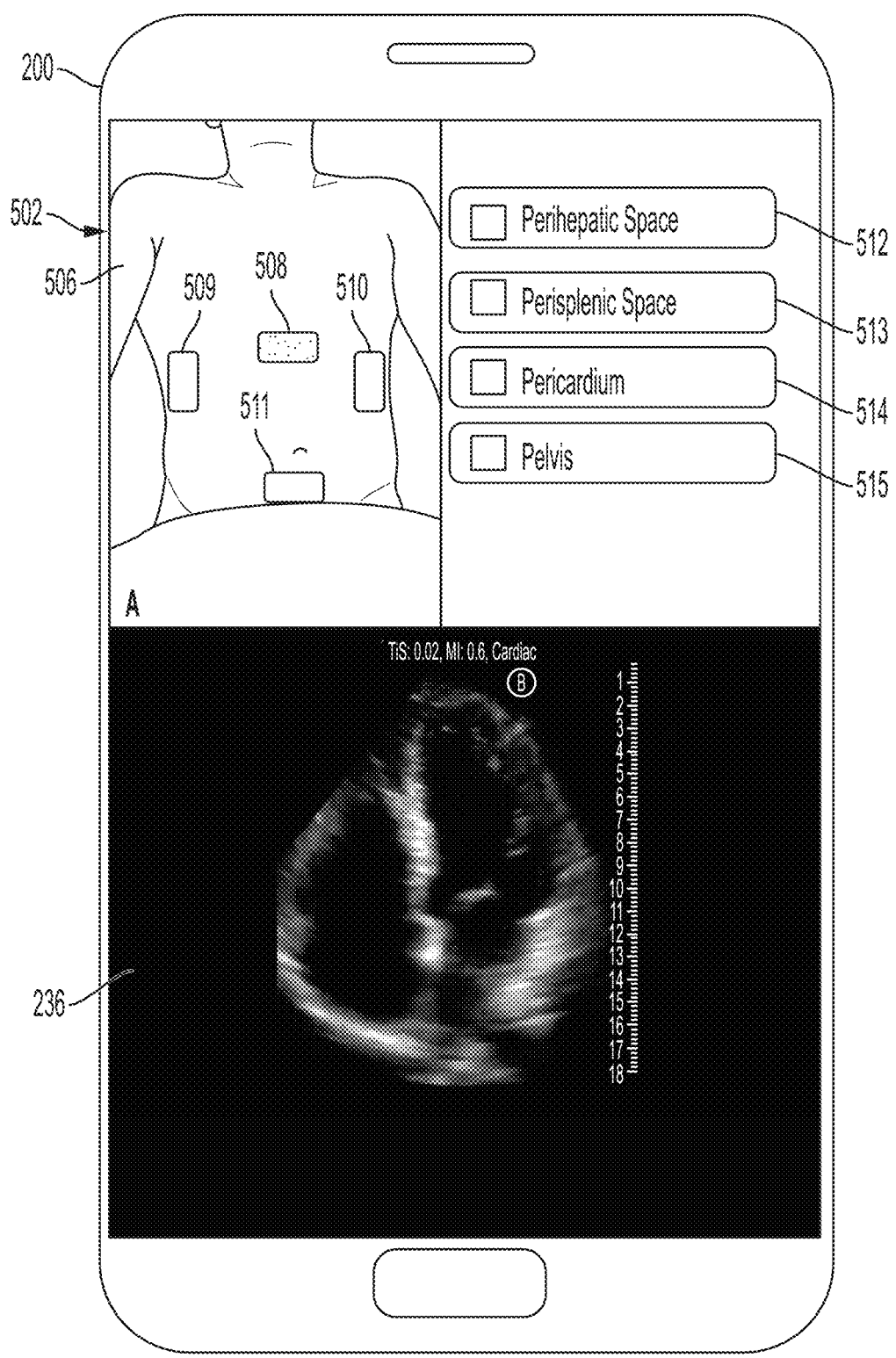
FIG. 12 illustrates an example display on a processing device displaying an indication of an anatomical location, in accordance with certain embodiments described herein.

FIG. 12 illustrates an example display on the processing device 200 displaying an indication of an anatomical location, in accordance with certain embodiments described herein. FIG. 12 is similar to FIG. 5, except that in FIG. 12, the marker 508 located at the pericardium on the frame of the video 502 of the subject is filled in. The filling in of the marker 508 may serve as an indication that the pericardium of the subject should be imaged next. Further description of displaying the first indication may be found with reference to act 106.

Figure 13:
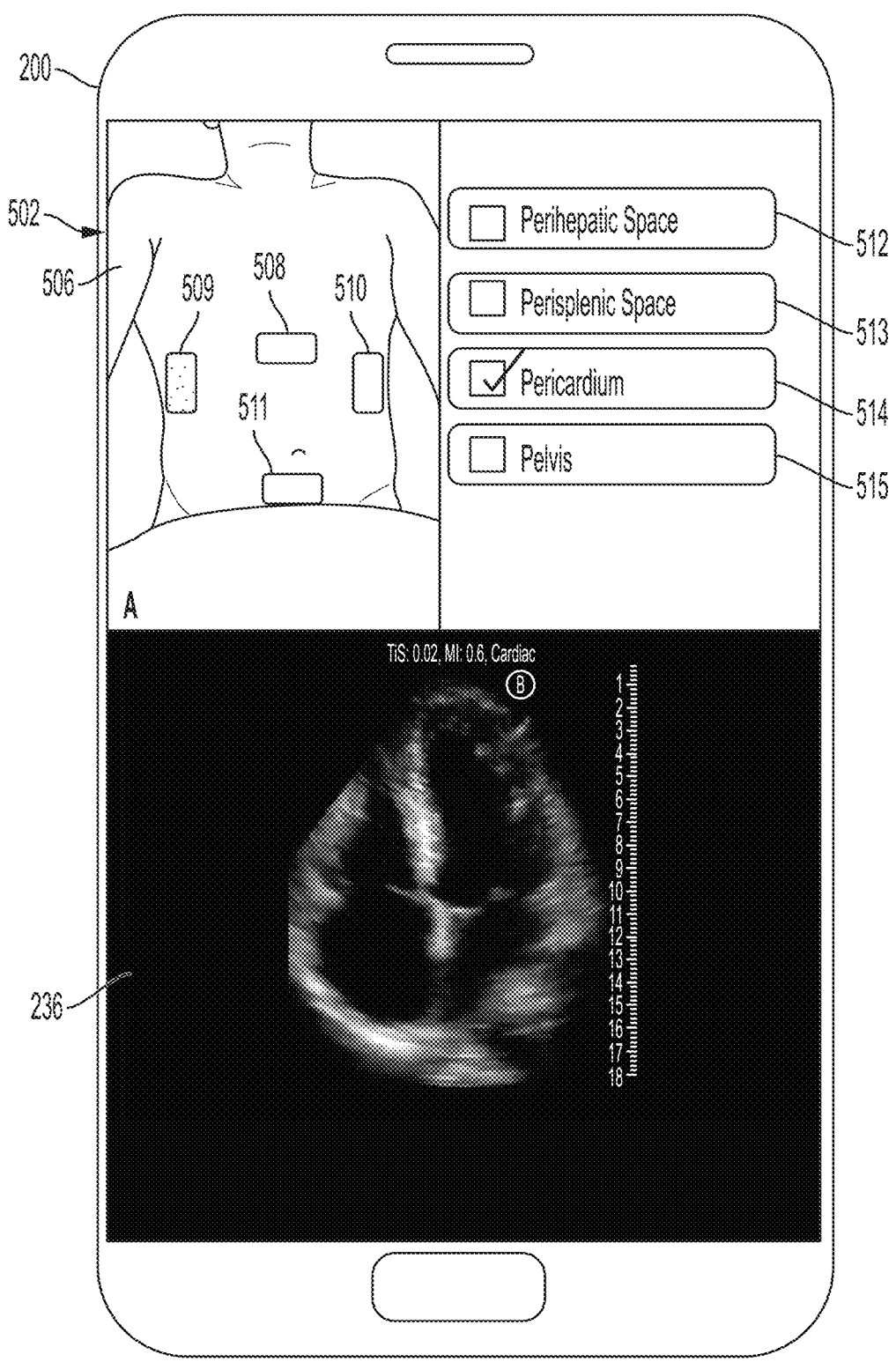
FIG. 13 illustrates an example display on a processing device simultaneously displaying two indications of two anatomical locations, in accordance with certain embodiments described herein.

FIG. 13 illustrates an example display on the processing device 200 simultaneously displaying two indications of two anatomical locations, in accordance with certain embodiments described herein. A checkmark is displayed in the checkbox option 514, which may serve as an indication that the pericardium of the subject has been imaged. Additionally, the marker 509 located at the perihepatic space in the frame of the video 502 of the subject is filled in, which may serve as an indication that the perihepatic space of the subject should be imaged next. Further description of displaying the second indication may be found with reference to act 112. As described with reference to act 110, the processing device may determine that the pericardium has been imaged by inputting the most recently collected ultrasound image 236 to a statistical model.

Figure 14:
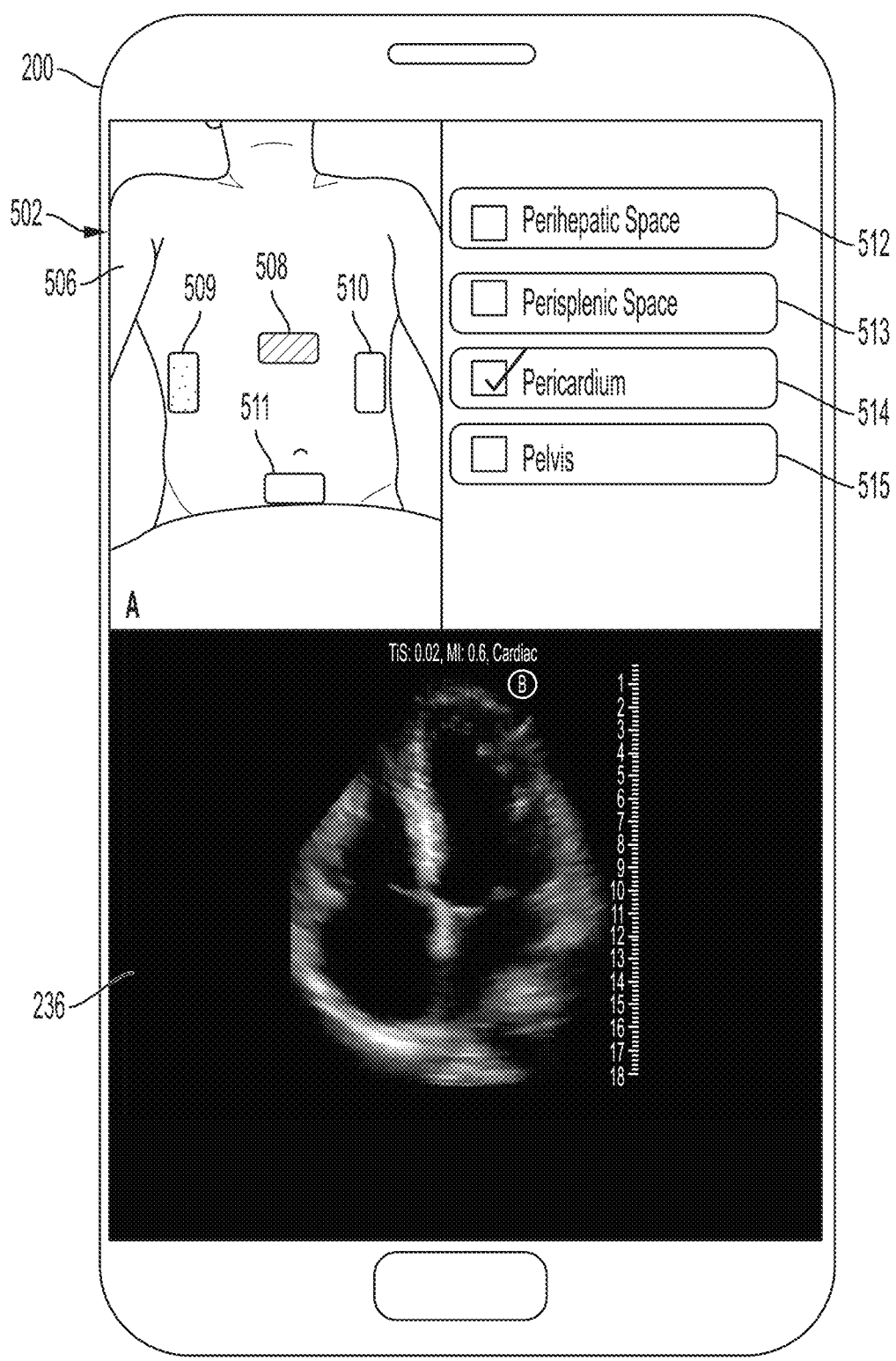
FIG. 14 illustrates an alternative to the display of FIG. 13, in accordance with certain embodiments described herein.

FIG. 14 illustrates an alternative to the display of FIG. 13, in accordance with certain embodiments described herein. In FIG. 14, the marker 508 located at the pericardium on the frame of the video 502 of the subject is filled in, but with a different shading than the filling in of the marker 509 located at the perihepatic space. In a similar manner as described with reference to FIG. 11, the filling in of the marker 508 with the different shading may serve as an indication that the pericardium has already been imaged. The marker 508 may remain filled in for the duration of the imaging session.

In any of the embodiments described herein, a statistical model may be stored on the processing device or on a remote server accessed by the processing device over a wireless or wired connection. The statistical model may be a convolutional neural network or other deep learning model, a random forest, a support vector machine, a linear classifier, and/or any other statistical model.

Figure 15:
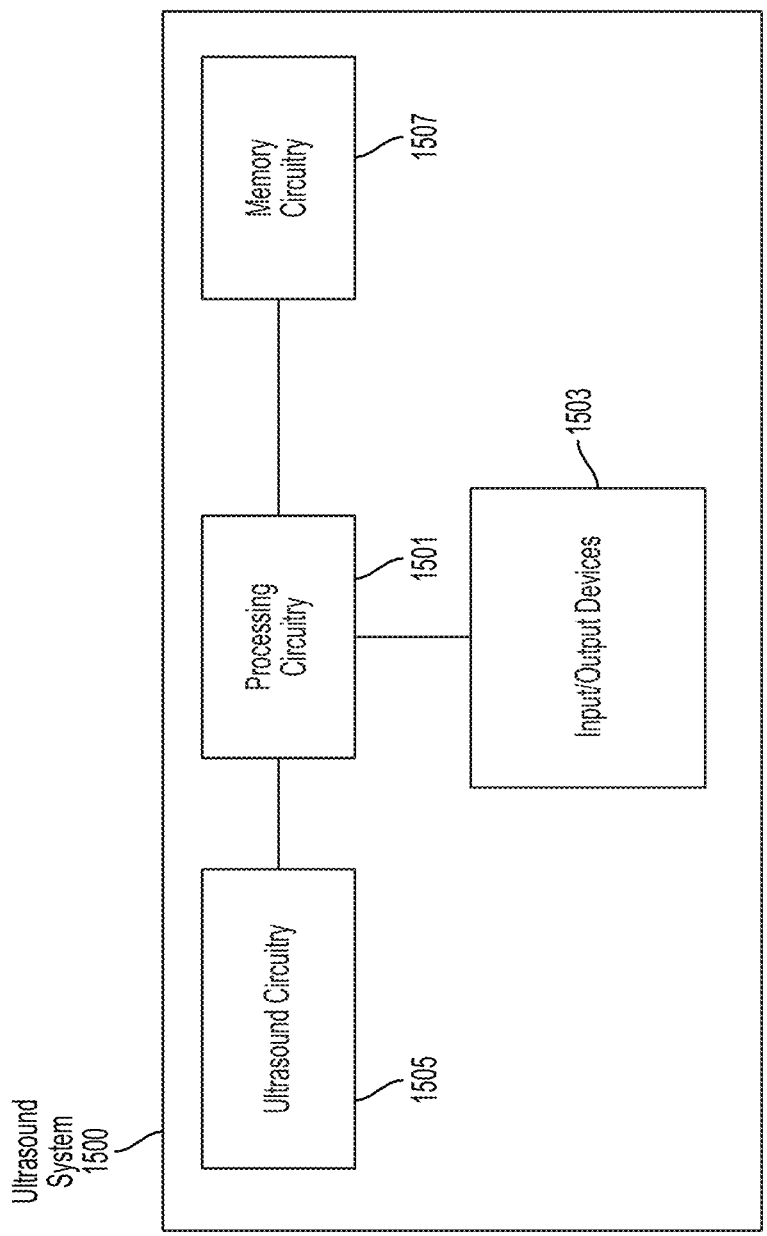
FIG. 15 shows a schematic block diagram illustrating aspects of an example ultrasound system upon which various aspects of the technology described herein may be practiced.

FIG. 15 shows a schematic block diagram illustrating aspects of an example ultrasound system 1500 upon which various aspects of the technology described herein may be practiced. For example, one or more components of the ultrasound system 1500 may perform any of the processes (e.g., the processes 100 or 800) described herein. As shown, the ultrasound system 1500 includes processing circuitry 1501, input/output devices 1503, ultrasound circuitry 1505, and memory circuitry 1507.

The ultrasound circuitry 1505 may be configured to generate ultrasound data that may be employed to generate an ultrasound image. The ultrasound circuitry 1505 may include one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 1505 (e.g., transmit circuitry, receive circuitry, control circuitry, power management circuitry, and processing circuitry) to form a monolithic ultrasound imaging device.

The processing circuitry 1501 may be configured to perform any of the functionality described herein. The processing circuitry 1501 may include one or more processors (e.g., computer hardware processors). To perform one or more functions, the processing circuitry 1501 may execute one or more processor-executable instructions stored in the memory circuitry 1507. The memory circuitry 1507 may be used for storing programs and data during operation of the ultrasound system 1500. The memory circuitry 1507 may include one or more storage devices such as non-transitory computer-readable storage media. The processing circuitry 1501 may control writing data to and reading data from the memory circuitry 1507 in any suitable manner.

In some embodiments, the processing circuitry 1501 may include specially-programmed and/or special-purpose hardware such as an application-specific integrated circuit (ASIC). For example, the processing circuitry 1501 may include one or more graphics processing units (GPUs) and/or one or more tensor processing units (TPUs). TPUs may be ASICs specifically designed for machine learning (e.g., deep learning). The TPUs may be employed to, for example, accelerate the inference phase of a neural network.

The input/output (I/O) devices 1503 may be configured to facilitate communication with other systems and/or an operator. Example I/O devices 1503 that may facilitate communication with an operator include: a keyboard, a mouse, a trackball, a microphone, a touch screen, a printing device, a display screen, a speaker, and a vibration device. Example I/O devices 1503 that may facilitate communication with other systems include wired and/or wireless communication circuitry such as BLUETOOTH, ZIGBEE, Ethernet, WiFi, and/or USB communication circuitry.

It should be appreciated that the ultrasound system 1500 may be implemented using any number of devices. For example, the components of the ultrasound system 1500 may be integrated into a single device. In another example, the ultrasound circuitry 1505 may be integrated into an ultrasound imaging device that is communicatively coupled with a processing device that includes the processing circuitry 1501, the input/output devices 1503, and the memory circuitry 1507.

Figure 16:
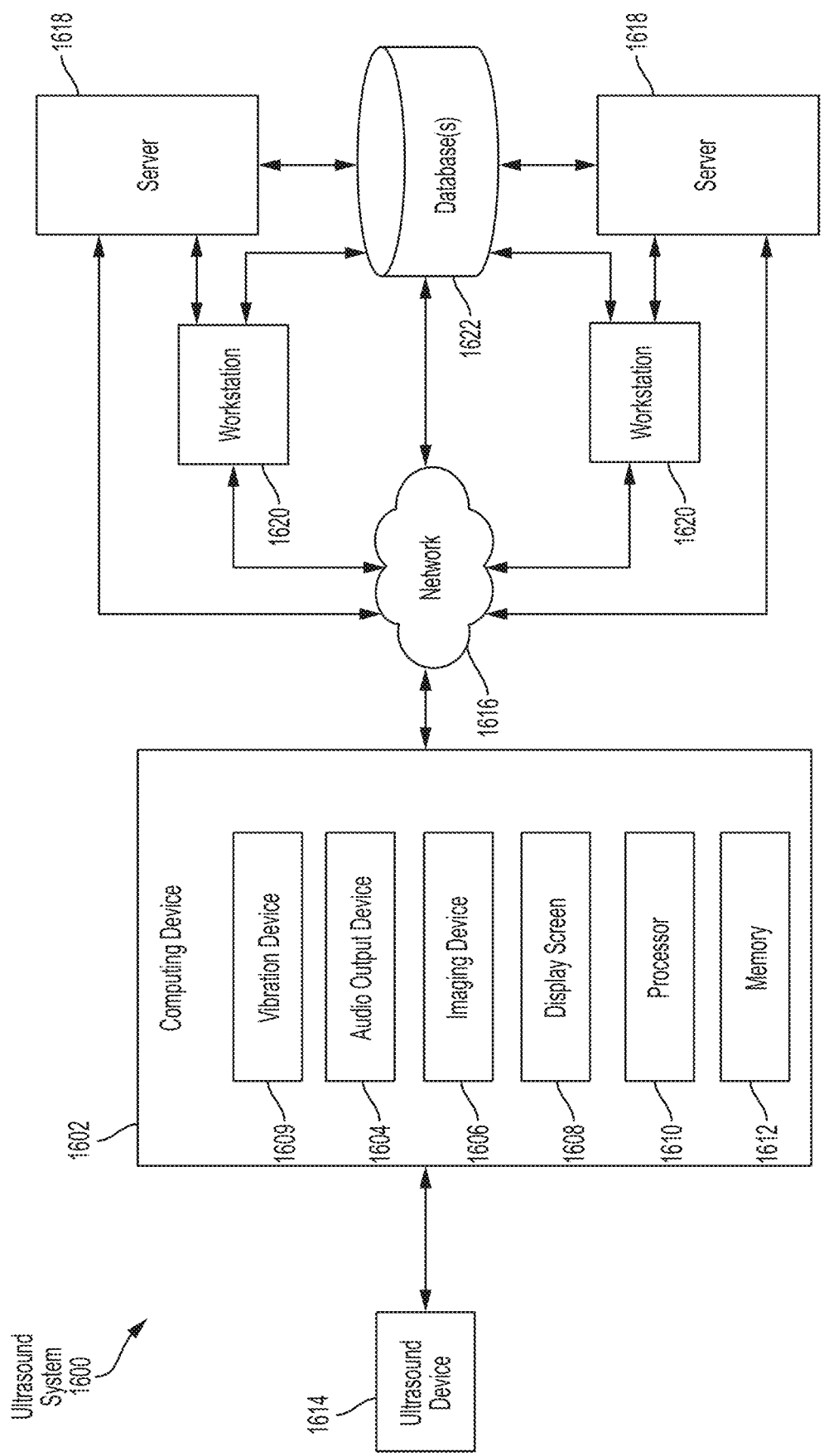
FIG. 16 shows a schematic block diagram illustrating aspects of another example ultrasound system upon which various aspects of the technology described herein may be practiced.

FIG. 16 shows a schematic block diagram illustrating aspects of another example ultrasound system 1600 upon which various aspects of the technology described herein may be practiced. For example, one or more components of the ultrasound system 1600 may perform any of the processes (e.g., the processes 100 or 800) described herein. As shown, the ultrasound system 1600 includes an ultrasound imaging device 1614 in wired and/or wireless communication with a processing device 1602 (which may correspond to the processing device 200). The processing device 1602 includes an audio output device 1604, an imaging device 1606, a display screen 1608, a processor 1610, a memory 1612, and a vibration device 1609. The processing device 1602 may communicate with one or more external devices over a network 1616. For example, the processing device 1602 may communicate with one or more workstations 1620, servers 1618, and/or databases 1622.

The ultrasound imaging device 1614 may be configured to generate ultrasound data that may be employed to generate an ultrasound image. The ultrasound imaging device 1614 may be constructed in any of a variety of ways. In some embodiments, the ultrasound imaging device 1614 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals by the transducer elements and the electrical signals are received by a receiver. The electrical signals representing the received echoes are sent to a receive beamformer that outputs ultrasound data.

The processing device 1602 may be configured to process the ultrasound data from the ultrasound imaging device 1614 to generate ultrasound images for display on the display screen 1608. The processing may be performed by, for example, the processor 1610. The processor 1610 may also be adapted to control the acquisition of ultrasound data with the ultrasound imaging device 1614. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the processing device 1602 may be configured to perform any of the processes (e.g., the processes 100 or 800) described herein (e.g., using the processor 1610). As shown, the processing device 1602 may include one or more elements that may be used during the performance of such processes. For example, the processing device 1602 may include one or more processors 1610 (e.g., computer hardware processors) and one or more articles of manufacture that include non-transitory computer-readable storage media such as the memory 1612. The processor 1610 may control writing data to and reading data from the memory 1612 in any suitable manner. To perform any of the functionality described herein, the processor 1610 may execute one or more processor-executable instructions stored in one or more non-transitory computer-readable storage media (e.g., the memory 1612), which may serve as non-transitory computer-readable storage media storing processor-executable instructions for execution by the processor 1610.

In some embodiments, the processing device 1602 may include one or more input and/or output devices such as the audio output device 1604, the imaging device 1606, the display screen 1608, and the vibration device 1609. The audio output device 1604 may be a device that is configured to emit audible sound such as a speaker. The imaging device 1606 may be configured to detect light (e.g., visible light) to form an image such as a camera. The display screen 1608 may be configured to display images and/or videos such as a liquid crystal display (LCD), a plasma display, and/or an organic light emitting diode (OLED) display. The vibration device 1609 may be configured to vibrate one or more components of the processing device 1602 to provide tactile feedback. These input and/or output devices may be communicatively coupled to the processor 1610 and/or under the control of the processor 1610. The processor 1610 may control these devices in accordance with a process being executed by the process 1610 (such as the processes 100 and 800). Similarly, the processor 1610 may control the audio output device 1604 to issue audible instructions and/or control the vibration device 1609 to change an intensity of tactile feedback (e.g., vibration) to issue tactile instructions. Additionally (or alternatively), the processor 1610 may control the imaging device 1606 to capture non-acoustic images of the ultrasound imaging device 1614 being used on a subject to provide an operator of the ultrasound imaging device 1614 an augmented reality interface.

It should be appreciated that the processing device 1602 may be implemented in any of a variety of ways. For example, the processing device 1602 may be implemented as a handheld device such as a mobile smartphone or a tablet. Thereby, an operator of the ultrasound imaging device 1614 may be able to operate the ultrasound imaging device 1614 with one hand and hold the processing device 1602 with another hand. In other examples, the processing device 1602 may be implemented as a portable device that is not a handheld device such as a laptop. In yet other examples, the processing device 1602 may be implemented as a stationary device such as a desktop computer.

In some embodiments, the processing device 1602 may communicate with one or more external devices via the network 1616. The processing device 1602 may be connected to the network 1616 over a wired connection (e.g., via an Ethernet cable) and/or a wireless connection (e.g., over a WiFi network). As shown in FIG. 16, these external devices may include servers 1618, workstations 1620, and/or databases 1622. The processing device 1602 may communicate with these devices to, for example, off-load computationally intensive tasks. For example, the processing device 1602 may send an ultrasound image over the network 1616 to the server 1618 for analysis (e.g., to identify an anatomical feature in the ultrasound) and receive the results of the analysis from the server 1618. Additionally (or alternatively), the processing device 1602 may communicate with these devices to access information that is not available locally and/or update a central information repository. For example, the processing device 1602 may access the medical records of a subject being imaged with the ultrasound imaging device 1614 from a file stored in the database 1622. In this example, the processing device 1602 may also provide one or more captured ultrasound images of the subject to the database 1622 to add to the medical record of the subject. For further description of ultrasound imaging devices and systems, see U.S. patent application Ser. No. 15/415,434 titled "UNIVERSAL ULTRASOUND IMAGING DEVICE AND RELATED APPARATUS AND METHODS," filed on Jan. 25, 2017 (and assigned to the assignee of the instant application), which is incorporated by reference herein in its entirety.

Aspects of the technology described herein relate to the application of automated image processing techniques to analyze images, such as ultrasound images or optical images. In some embodiments, the automated image processing techniques may include machine learning techniques such as deep learning techniques. Machine learning techniques may include techniques that seek to identify patterns in a set of data points and use the identified patterns to make predictions for new data points. These machine learning techniques may involve training (and/or building) a model using a training data set to make such predictions. The trained model may be used as, for example, a classifier that is configured to receive a data point as an input and provide an indication of a class to which the data point likely belongs as an output.

Deep learning techniques may include those machine learning techniques that employ neural networks to make predictions. Neural networks typically include a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input, for example, to weight some inputs higher than others. Example transfer functions that may be employed include step functions, piecewise linear functions, and sigmoid functions. These neurons may be organized into a plurality of sequential layers that each include one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may include a set of example inputs and an answer associated with each input. For example, the training data may include a plurality of ultrasound images or sets of raw acoustical data that are each labeled with an anatomical feature that is contained in the respective ultrasound image or set of raw acoustical data. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

Once the training data has been created, the training data may be loaded to a database (e.g., an image database) and used to train a neural network using deep learning techniques. Once the neural network has been trained, the trained neural network may be deployed to one or more processing devices. It should be appreciated that the neural network may be trained with any number of sample patient images, although it will be appreciated that the more sample images used, the more robust the trained model data may be.

Figure 17:
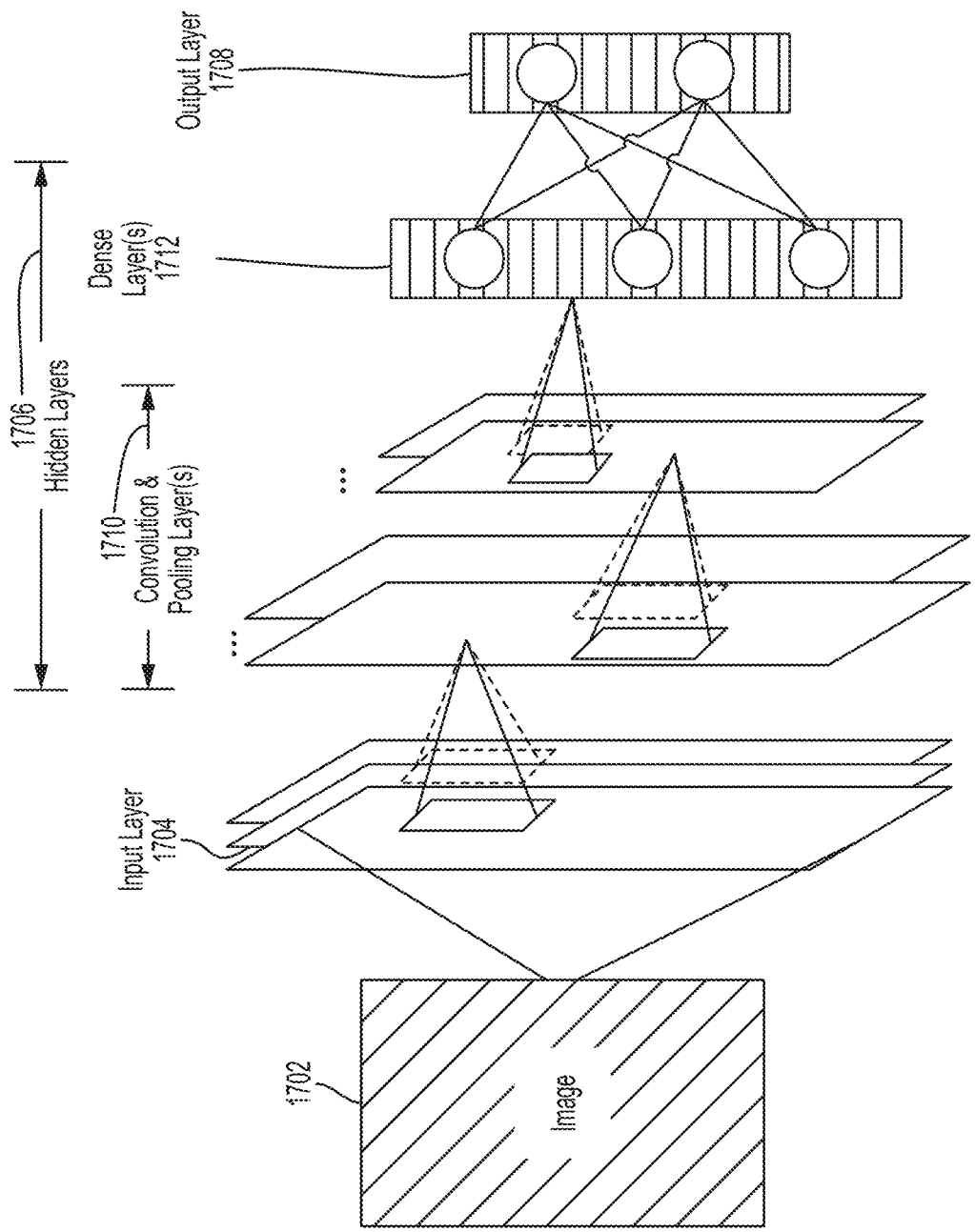
FIG. 17 illustrates an example convolutional neural network that is configured to analyze an image.

In some applications, a neural network may be implemented using one or more convolution layers to form a convolutional neural network. An example convolutional neural network is shown in FIG. 17 that is configured to analyze an image 1702. As shown, the convolutional neural network includes an input layer 1704 to receive the image 1702, an output layer 1708 to provide the output, and a plurality of hidden layers 1706 connected between the input layer 1704 and the output layer 1708. The plurality of hidden layers 1706 includes convolution and pooling layers 1710 and dense (e.g., fully connected) layers 1712.

The input layer 1704 may receive the input to the convolutional neural network. As shown in FIG. 17, the input the convolutional neural network may be the image 1702. The image 1702 may be, for example, an ultrasound image.

The input layer 1704 may be followed by one or more convolution and pooling layers 1710. A convolutional layer may include a set of filters that are spatially smaller (e.g., have a smaller width and/or height) than the input to the convolutional layer (e.g., the image 1702). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 1710 may be followed by dense layers 1712. The dense layers 1712 may include one or more layers each with one or more neurons that receives an input from a previous layer (e.g., a convolutional or pooling layer) and provides an output to a subsequent layer (e.g., the output layer 1708). The dense layers 1712 may be described as "dense" because each of the neurons in a given layer may receive an input from each neuron in a previous layer and provide an output to each neuron in a subsequent layer. The dense layers 1712 may be followed by an output layer 1708 that provides the output of the convolutional neural network. The output may be, for example, an indication of which class, from a set of classes, the image 1702 (or any portion of the image 1702) belongs to.

It should be appreciated that the convolutional neural network shown in FIG. 17 is only one example implementation and that other implementations may be employed. For example, one or more layers may be added to or removed from the convolutional neural network shown in FIG. 17. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

For further description of deep learning techniques, see U.S. patent application Ser. No. 15/626,423 titled "AUTOMATIC IMAGE ACQUISITION FOR ASSISTING A USER TO OPERATE AN ULTRASOUND IMAGING DEVICE," filed on Jun. 19, 2017 (and assigned to the assignee of the instant application), which is incorporated by reference herein in its entirety. In any of the embodiments described herein, instead of/in addition to using a convolutional neural network, a fully connected neural network may be used. Additionally, while processing of ultrasound images using deep learning techniques is described with reference to FIG. 17, the description may apply equally to processing of optical images.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An apparatus, comprising:
   a processing device in operative communication with an ultrasound device and configured to:
      receive first ultrasound data collected from a subject by the ultrasound device wherein the first ultrasound data includes raw acoustical data collected by an ultrasound transducer and representing scan lines and/or an ultrasound image of an anatomical feature of a patient;

automatically determine, based on the first ultrasound data having been collected by an ultrasound transducer and representing scan lines and/or an ultrasound image, a first anatomical location on the subject from which at least some of the first ultrasound data was collected; and display a first indication of the first anatomical location, wherein the processing device is configured, to display the first indication, as a marker within a non-ultrasound image or video that was not displayed prior to automatically determining the first anatomical location on the subject from which at least some of the first ultrasound data was collected.

2. An apparatus, comprising:
a processing device in operative communication with an ultrasound device and configured to:
receive first ultrasound data collected from a subject by the ultrasound device wherein the first ultrasound data includes raw acoustical data collected by an ultrasound transducer and representing scan lines and/or an ultrasound image of an anatomical feature of a patient;
automatically determine, based on the first ultrasound data having been collected by an ultrasound transducer and representing scan lines and/or an ultrasound image, a first anatomical location on the subject from which at least some of the first ultrasound data was collected; and
display, on a non-ultrasound image or video, a first indication of the first anatomical location, wherein the processing device is configured, when displaying the first indication, to modify a marker that was displayed within said non-ultrasound image or video prior to automatically determining the first anatomical location on the subject from which at least some of the first ultrasound data was collected.

3. An apparatus, comprising:
a processing device in operative communication with an ultrasound device and configured to:
receive first ultrasound data collected from a subject by the ultrasound device wherein the first ultrasound data includes raw acoustical data collected by an ultrasound transducer and representing scan lines and/or an ultrasound image of an anatomical feature of a patient;
automatically determine, based on the first ultrasound data having been collected by an ultrasound transducer and representing scan lines and/or an ultrasound image, a first anatomical location on the subject from which at least some of the first ultrasound data was collected; and
display, on a non-ultrasound image or video, a first indication of the first anatomical location, wherein the processing device is configured, when displaying the first indication, to display or modify a marker on an image of a body or a body portion within the non-ultrasound image or video such that the marker appears in the image of the body or body portion to be located at the first anatomical location on the subject.

4. The apparatus of claim 3, wherein the image of the body or body portion does not change as the processing device moves.

5. An apparatus, comprising:
a processing device in operative communication with an ultrasound device and configured to:
receive first ultrasound data collected from a subject by the ultrasound device wherein the first ultrasound data includes raw acoustical data collected by an ultrasound transducer and representing scan lines and/or an ultrasound image of an anatomical feature of a patient;
automatically determine, based on the first ultrasound data having been collected by an ultrasound transducer and representing scan lines and/or an ultrasound image, a first anatomical location on the subject from which at least some of the first ultrasound data was collected; and
display, on a non-ultrasound image or video, a first indication of the first anatomical location, wherein the processing device is configured, when displaying the first indication, to display or modify text within the non-ultrasound image or video describing the first anatomical location.

6. The apparatus of claim 5, wherein the processing device is configured, when displaying the first indication, to display a symbol next to the text describing the first anatomical location.

7. The apparatus of claim 5, wherein the processing device is configured, when displaying the first indication, to strike through the text describing the first anatomical location.

8. An apparatus, comprising:
a processing device in operative communication with an ultrasound device and configured to:
receive first ultrasound data collected from a subject by the ultrasound device wherein the first ultrasound data includes raw acoustical data collected by an ultrasound transducer and representing scan lines and/or an ultrasound image of an anatomical feature of a patient;
automatically determine, based on the first ultrasound data having been collected by an ultrasound transducer and representing scan lines and/or an ultrasound image, a first anatomical location on the subject from which at least some of the first ultrasound data was collected; and
display, on a non-ultrasound image or video, a first indication of the first anatomical location,
wherein the processing device is further configured to:
receive, by the processing device, second ultrasound data collected from the subject by the ultrasound device wherein the second ultrasound data includes raw acoustical data collected by the ultrasound transducer and representing scan lines and/or an ultrasound image of an anatomical feature of a patient;
automatically determine, based on the second ultrasound data, a second anatomical location on the subject from which at least some of the second ultrasound data was collected; and
simultaneously display the first indication of the first anatomical location and a second indication of the second anatomical location.

* * * * *